United States Patent [19]

Johnson

[11] Patent Number: 5,851,786
[45] Date of Patent: Dec. 22, 1998

[54] PRODUCT AND PROCESS TO REGULATE ACTIN POLYMERIZATION

[75] Inventor: Gary L. Johnson, Boulder, Colo.

[73] Assignee: National Jewish Center For Immunology and Respiratory Medicine, Denver, Colo.

[21] Appl. No.: 534,694

[22] Filed: Sep. 27, 1995

[51] Int. Cl.[6] .............................. C12Q 1/02; C12Q 1/37; C12Q 1/00; G01N 33/53
[52] U.S. Cl. ................................. 435/29; 435/23; 435/21; 435/65.1; 435/69.1; 435/69.2; 435/17; 435/4; 435/975; 435/968; 435/7.1; 435/7.2; 435/7.21; 435/7.23; 435/7.24; 424/278.1; 424/94.1; 424/94.5
[58] Field of Search .................................. 435/29, 23, 21, 435/68.1, 69.1, 69.2, 17, 4, 975, 968, 7.1, 7.2, 7.21, 7.23, 7.24; 424/278.1, 94.1, 94.5

[56] References Cited

U.S. PATENT DOCUMENTS 5,366,889 11/1994 MacDonald et al. ........................ 435/6

FOREIGN PATENT DOCUMENTS

WO 92/05244 A1 4/1992 WIPO.

OTHER PUBLICATIONS

Cuttitta et al., 1985, Nature, 316:823–826 Month Not Available.
Baffy et al., 1994, J. Biol. Chem., 269(11);8483–8487 Month Not Available.
Chambard et al., 1987, Nature, 326:800–803 Month Not Available.
Fukumoto al., 1990, Oncogene, 5:1321–1328 Month Not Available.
Hung et al., 1992, J. Biol. Chem., 267(29):20831–20834 Month Not Available.
Khosravi–Far et al., 1994, Mol. Cell. Biol., 14(10):6848–6857 Month Not Available.
Paterson et al., 1990, J. Cell Biol., 111:1001–1007 Month Not Available.
Ridley, 1994, J. Cell Science, Supp. 18:127–131 Month Not Available.
Ridley et al., 1994, EMBO J., 13(11):2600–2610 Month Not Available.
Ridley et al., 1993, EMBO J., 12(13):5151–5160 Month Not Available.
Ridley et al., 1992, Cell, 70:389–399 Month Not Available.
Rozengurt et al., 1983, Proc. Natl. Acad. Sci. USA, 80:2936–2940 Month Not Available.
van Corven et al., 1993, Proc. Natl. Acad. Sci. USA, 90:1257–1261 Month Not Available.
van Corven et al., 1989, Cell, 59:45–54 Month Not Available.
Zheng et al., 1995, J. Biol. Chem., 270(16):9031–9034 Month Not Available.

Primary Examiner—Louise Leary
Attorney, Agent, or Firm—Lahive & Cockfield, LLP; Giulio A. DeConti, Jr.; Catherine J. Kara

[57] ABSTRACT

The present invention relates to methods useful for identifying compounds capable of specifically regulating actin polymerization, stress fiber formation or focal adhesion assembly by regulating $G_{\alpha 12}$ and/or $G_{\alpha 13}$ activity in cells involved in inflammatory responses, immune responses, allergic responses and neuronal responses, kits to perform such assays and methods to control disease related to such responses.

43 Claims, 6 Drawing Sheets

PRODUCT AND PROCESS TO REGULATE ACTIN POLYMERIZATION

GOVERNMENT RIGHTS

This invention was made in part with government support under GM-30324, awarded by the National Institutes of Health. The government has certain rights to this invention.

FIELD OF THE INVENTION

The present invention relates to a process for identifying compounds that regulates stress fiber formation. In particular, the present invention relates to an assay and methods useful for identifying compounds that specifically regulate the activation of Rho protein in response to external stimuli.

BACKGROUND OF THE INVENTION

Cells have a cytoskeletal network that is associated with the plasma membrane of the cell. The cytoskeleton is comprised of a dense network of actin filaments and associated actin-binding proteins. Components of both the cytoskeletal network and the plasma membrane are important for cell signalling. Alterations in a cell cytoskeleton accompanies a variety of cell processes, including cell shape and regulatory responses including chemotaxis and mitogenesis. Such alterations are characterized by changes in cell morphology and cell surface topology due, in part, to the formation of three types of structures that contain actin filaments, stress fibers, pseudopodia and membrane ruffles. Stress fibers are bundles of actin filaments that terminate at one end at the plasma membrane in a focal adhesion. Membrane ruffles comprise a dense network of cross-linked actin filaments. Pseudopodia are membrane protrusions containing actin filaments involved in cell migration.

A variety of diseases result from uncontrolled cell growth control and motility. For example, in a variety of inflammatory diseases, activated neutrophils recruited to certain tissues release superoxide anions and proteolytic enzymes that damage or destroy tissue. In addition, cancer development results from progressive cell growth and metastases upon transformation of the cell by oncogenic proteins. In both cases, cytoskeletal rearrangement enables cells to grow or infiltrate certain tissues, thereby causing damage to such tissues. As such, modulation of cytoskeletal rearrangement to regulate such growth and motility can be useful in the treatment of disease.

Compounds can be developed that regulate the activity of molecules involved in biological functions, such as stress fiber formation or the assembly of focal adhesions. Development of such compounds, therefore, is dependent upon understanding the molecules involved in such functions. Previous work has shown that Rho protein regulates actin polymerization resulting in the formation of stress fibers and the assembly of focal adhesions (see, Paterson et al., *J. Exp. Med.* 111:1001–1007, 1991; Ridley et al., *Cell* 70:389–399, 1992; Ridley et al., *EMBO J.* 13:2600–2610, 1994 (a) ; and Ridley et al., *J. Cell Science Supplement* 18:127–131, 1994 (b)). Furthermore, receptors for lysophosphatidic acid (LPA), gastrin releasing peptide (GRP), bradykinin and thrombin have been shown to stimulate Rho-dependent stress fiber and focal adhesion formation (see, Ridley et al., ibid., 1992; and Ridley et al., ibid., 1994(b)). Receptors for LPA and GRP, for example, have been shown to be coupled to heterotrimeric G proteins (see, van Corven et al, i Cell 59:45–54, 1989; and Rozengurt et al., *Proc. Natl. Acad. Sci. USA* 80:2936–2940, 1983). Prior investigators, however, have failed to teach that actin polymerization, focal adhesion assembly and stress fiber formation are regulated by Rho protein, which in turn is regulated by G proteins or tyrosine kinases.

Despite a long-felt need to discover compounds for regulating actin polymerization, stress fiber formation and focal adhesion assembly in cells, the complexity of signal transduction networks in a cell has hindered the development of rapid and efficient methods for identifying compounds capable of regulating cytoskeletal rearrangements. Accordingly, there remains a need to develop efficient methods for identifying compounds capable of specifically regulating stress fiber formation and focal adhesion assembly. Such compounds would permit regulation of specific steps of a signal transduction pathway leading to stress fiber formation and focal adhesion assembly, thus enabling the treatment of various diseases involving the migration or growth of cells.

SUMMARY OF THE INVENTION

The present invention provides a solution to the complex problem of identifying regulatory compounds which can be used to regulate cellular function, including actin polymerization, stress fiber formation and/or focal adhesion assembly. Despite the complexity of signal transduction networks in cells, the present invention provides for an efficient method for identifying compounds capable of specifically regulating Rho protein activity. In particular, the present invention provides a method to the identify compounds that inhibit activation of Rho protein by $G_{\alpha 12}$ and/or $G_{\alpha 13}$ proteins. Those of skill in the art will immediately recognize the advantages arising from this invention which include the identification and uses of compounds which are useful for the treatment of a wide range of diseases.

One embodiment of the present invention includes a method to identify compounds capable of regulating actin polymerization, stress fiber formation or focal adhesion assembly in a cell, comprising: (1) contacting a cell with a putative regulatory compound, wherein the cell includes a Rho protein and a G protein that can regulate the activity of the Rho protein; and (2) assessing the ability of the putative regulatory compound to regulate a biological function selected from the group consisting of actin polymerization, stress fiber formation or focal adhesion assembly. The assessment step preferably involves determining the ability of the G protein to regulate Rho protein activity in the cell. Preferred G proteins for use with the present method include $G_{\alpha 12}$ and/or $G_{\alpha 13}$.

Another embodiment of the present invention includes a method to identify compounds capable of regulating actin polymerization, stress fiber formation or focal adhesion assembly in a cell, comprising: (1) contacting a putative regulatory compound with a formulation comprising a Rho regulator molecule and a G protein capable of regulating the activity of the Rho regulator molecule; and (2) assessing the ability of the putative regulatory compound to regulate the activity of the Rho regulator molecule. The assessment step preferably involves determining the binding of the G protein to the Rho regulator molecule.

The present invention also includes a method to inhibit a biological function including actin polymerization, stress fiber formation and focal adhesion assembly, comprising inhibiting the activity of $G_{\alpha 12}$ and/or $G_{\alpha 13}$. In particular, the present invention includes a method to inhibit cell metastases or chemotaxis by inhibiting the activity of $G_{\alpha 12}$ and/or $G_{\alpha 13}$. The activity is preferably inhibited by requestering a $G_{\alpha 12}$ or a $G_{\alpha 13}$ protein in active complex, regulating the nucleotide exchange region of $G_{\alpha 12}$ or $G_{\alpha 13}$ protein, regulating a cell surface receptor interaction with $G_{\alpha 12}$ or a $G_{\alpha 13}$ protein, regulating the interaction between $G_{\alpha 12}$ or $G_{\alpha 13}$ protein with a Rho regulator molecule, regulating the expression of endogenous or heterologous nucleic acid molecules encoding a $G_{\alpha 12}$ or $G_{\alpha 13}$ protein, or combustions thereof.

One aspect of the present invention uncludes a method to identify compounds capable of regulating action polymerization, stress fiber formation or focal adhesion asembly in a cell, comprising: (1) contacting a cell a putative regulatory compound, wherin the cell includes a Rho protein and a first protein including a G protein and a tyrosine kinase; and (2) assessing the ability of the putative regulatory compound to regulate a biological function including actin polymerization, stress fiber formation and focal adhesion assembly in the cell by determining the ability of the first protein to regulate Rho protein activity in the cell.

Another aspect of the present invention includes a method to identity compounds capable of regulating actin polymerization, stress fiber formation or focal adhesion assembling, comprising: (1) contacting a first protein including a G protein a tyrosine kinase, and a second protein comprising a Rho regulator molecule, with a putative regulatory compound; and (2) assessing the ability of the putative regulatory compound to regulate the activity of the Rho regulator molecule.

Yet another aspect of the present invention includes a method to treat an animal with a disease including cancer, respiratory distress syndrome, inflammatory bowel disease, Parkinson's disease, Alzheimer's disease and restenosis, the method comprising administering to an animal an effective amount of a therapeutic composition comprising a compound that regulates a biological function including actin polymerization, stress fiber formation or focal adhesion assembly.

The present invention also includes a kit to identify compounds capable of regulating actin polymerization, stress fiber formation or focal adhesion assembly, the kit comprising: (1) a cell comprising a Rho protein and a protein including a G protein and/or a tyrosine kinase; and (2) a means for detecting regulation of the Rho protein.

DETAILED DESCRIPTION

The present invention relates to a method for identifying compounds that regulate actin polymerization, stress fiber formation and/or focal adhesion assembly and products identified using such method. Actin polymerization refers to the polymerization of actin monomers to form actin polymers. A particular structure of a cytoskeleton is referred to as a stress fiber. As used herein, the term "stress fiber" refers to a cellular structure comprising bundles of actin filaments as generally described in Darnell et al. (*Molecular Cell Biology*, Scientific American Books, 1990, which is incorporated herein by reference in its entirety). As used herein, the term "cytoskeleton" refers to a structure comprising protein fibers, including actin microfilaments, microtubules and/or intermediate filaments. Another structure of a cytoskeleton is referred to as a focal adhesion or an adhesion plaque. As used herein, the phrase "focal adhesion" or "adhesion plaque" refers to points of contact between actin filaments and the plasma membrane of a cell (generally described in Darnell et al., ibid.).

The polymerization and depolymerization of cytoskeletal filaments can be regulated by molecules involved in a signal transduction pathway in a cell. As used herein, the phrase "signal transduction pathway" refers to at least one biochemical reaction, but more commonly a series of biochemical reactions, which result from interaction of a cell with a stimulatory compound. The interaction of a stimulatory compound with a cell generates a "signal" that is transmitted through a signal transduction pathway, ultimately resulting in stress fiber formation and/or focal adhesion assembly. Compounds inhibitory to signal transduction pathways (antagonists) are also useful and can be identified by the methods of the present invention.

A signal transduction pathway of the present invention can include a variety of signal transduction molecules that play a role in the transmission of a signal from one portion of a cell to another portion of a cell. As used herein, the term "molecule" refers to a protein, a lipid, a nucleic acid or an ion, and at times is used interchangeably with such terms. In particular, a signal transduction molecule refers to a protein, a lipid, a nucleotide, or an ion involved in a signal transduction pathway. Signal transduction molecules of the present invention include, for example, cell surface receptors and intracellular signal transduction molecules. As used herein, the phrase "cell surface receptor" includes molecules and complexes of molecules capable of receiving a signal and the transmission of such a signal across the plasma membrane of a cell. The phrase "intracellular signal transduction molecule," as used herein, includes those molecules or complexes of molecules involved in transmitting a signal from the plasma membrane of a cell through the cytoplasm of the cell, and in some instances, into the cell's nucleus. The phrase "stimulatory compound" as used herein, includes ligands capable of binding to cell surface receptors to initiate a signal transduction pathway, as well as intracellular initiator molecules capable of initiating a signal transduction pathway from inside a cell.

One aspect of the present invention includes a cell-based assay to identify compounds, referred to herein as "putative regulatory compounds", which are capable of regulating actin polymerization, stress fiber formation and/or focal adhesion assembly. As used herein, the term "putative" refers to compounds having an unknown or previously unappreciated regulatory activity in a particular process. As such, the term "identify" is intended to include all compounds, the usefulness of which as a regulatory compound of actin polymerization, stress fiber formation and/or focal adhesion assembly is determined by a method of the present invention.

One embodiment of the present invention relates to a method to identify a putative regulatory compound that regulates actin polymerization, stress fiber formation and/or focal adhesion assembly in a cell, comprising: (1) contacting a cell with a putative regulatory compound, wherein the cell includes a Rho protein and a G protein that can regulate the activity of the Rho protein; and (2) assessing the ability of the putative regulatory compound to regulate a biological function including actin polymerization, stress fiber formation and/or focal adhesion assembly.

Suitable cells for use with the present invention include any cell that has a G protein and a Rho protein. Such cells can include normal cells or transformed cells (i.e., with a heterologous nucleic acid molecule) that express a receptor in a native physiological context (e.g., smooth muscle cells, endothelial cells, epithelial cells, basophils, mast cells, eosinophils, neutrophils, macrophages, lymphocytes, dendritic cells, natural killer cells, plasma cells, neuroblasts, stem cells and cancer cells). Alternatively, cells for use with the present invention can include spontaneously occurring variants of normal cells, or genetically engineered cells, that have altered signal transduction activity, such as enhanced responses to particular ligands. Signal transduction variants of normal cells can be identified using methods known to those in the art. For example, variants can be selected using fluorescence activated cell sorting (FACS) based on the level of calcium mobilization by a cell in response to a ligand. Genetically engineered cells can include recombinant cells of the present invention (described in detail below) that have been transformed with, for example, a recombinant molecule encoding a signal transduction molecule of the present invention.

Cells for use with the present invention include mammalian, invertebrate, plant, insect, fungal, yeast and bacterial cells. Preferred cells include mammalian, amphibian and yeast cells. Preferred mammalian cells include primate, mouse and rat, with HELA, Swiss 3T3, fibroblast, rat basophilic, human eosinophil, human endothelial, human T cell, human B cell, human neutrophil, human macrophage, human epithelial, melanocyte, leukemia, MonoMac6, Rat la, HEK 293, KU812 and BJAB cells being more preferred.

In one embodiment, a cell suitable for use in the present invention has at least one type of cell surface receptor. A cell surface receptor as referred to herein includes those cell surface receptors capable of binding to a ligand (as described in detail below) and capable of initiating a signal transduction pathway in a cell upon ligand binding. A cell surface receptor typically includes an external portion located on the outer surface of a plasma membrane of a cell, a transmembrane portion that spans the plasma membrane, and a cytoplasmic portion located on the inner surface of the plasma membrane.

A cell surface receptor as described herein can be produced by expression of a naturally occurring gene encoding a cell surface receptor and/or a heterologous nucleic acid molecule transformed into a cell. Examples of cell surface receptors include, but are not limited to, G protein-linked receptors, tyrosine kinase-linked receptors and receptors having ligand-gated ion channels. Preferred G protein-linked receptors of the present invention include serpentine receptors which contain seven transmembrane spanning segments and interact with G-proteins via their cytoplasmic domains. More preferred G-protein-linked receptors include chemoattractant, chemokine, adenylyl cyclase-coupled, muscarinic acetylcholine, catecholamine, and neuropeptide receptors. Even more preferred G-protein-linked receptors include thrombin receptors, lysophosphatidate receptors (LPAR), C5a receptors (C5aR), interleukin-8 receptors (IL-8R), monocyte chemotactic protein $1\alpha$ receptors (MIP$1\alpha$R), monocyte chemotactic protein $1\beta$ receptors (MIP$1\beta$R), monocyte chemoattractant protein 1 receptors (MCP-1R), monocyte chemoattractant protein 3 receptors (MCP-3R), platelet activating factor receptors (PAFR), N-Formyl-methionyl-leucyl-[$^{3H}$] phenylalanine receptors (FMLPR), leukotriene $B_4$ receptors (LTB$_4$R), gastrin releasing peptide (GRP) receptors (GRPR) (including bombesin receptors), RANTES receptors, Substance P receptors, vasopressin receptors and bradykinin receptors. Preferred tyrosine kinase-linked receptors of the present invention include, but are not limited to, receptors linked to abl or BCR-abl, Fc$\epsilon$RI$\beta$, Fc$\gamma$RI, Fc$\gamma$RIII, Fc$\gamma$RIIA, Fc$\alpha$R, T cell receptors (TCR) and B cell receptors (BCR). Preferred cells of the present invention have a cell surface receptor, such as a C5aR, a Rantes receptor, an LPAR, a GRPR, a thrombin receptor, an IL-8R, a Substance P receptor, a vasopressin receptor and/or a bradykinin receptor.

In another embodiment, a cell suitable for use in the present invention has one or more intracellular signal transduction molecules capable of transmitting a signal through the cytoplasm of the cell, resulting in actin polymerization, stress fiber formation and/or focal adhesion assembly. An intracellular signal transduction molecule as described herein can be produced in a cell by expression of a naturally occurring gene and/or by expression of a heterologous nucleic acid molecule transformed into the cell.

A preferred cell of the present invention has, amongst other signal transduction molecules, G proteins, tyrosine kinases, low molecular weight G protein regulatory molecules and/or low molecular weight G proteins. Suitable G proteins of the present invention include a G protein capable of regulating the activity of a Rho regulator molecule, such as enhancing or limiting the ability of a Rho regulator molecule to stimulate the guanine nucleotide exchange activity of Rho. As used herein, the phrase "guanine nucleotide binding" refers to guanine nucleotide binding to a guanine nucleotide binding site of a G protein. Guanine nucleotides include guanine triphosphate (GTP), guanine diphosphate (GDP) and guanine monophosphate (GMP). The phrase "guanine nucleotide exchange" refers to the loss of a phosphate from a guanine nucleotide. For example, "guanine nucleotide exchange" includes the exchange of GDP for GTP. Guanine nucleotide binding to a G protein can be determined using a GTP binding assay, such as an assay described in Vaillancourt et al. (*Methods of Enzymology* 238:255–258, 1994, which is incorporated herein by reference in its entirety) or an assay known to those skilled in the art. Guanine nucleotide exchange by a G protein can be determined using a GTP exchange assay, such as an assay described in Vaillancourt et al. (ibid.) or an assay known to those skilled in the art.

Preferred G proteins of the present invention include trimeric G proteins having an $\alpha$ subunit capable of binding GDP or GTP, and a $\beta$ and $\gamma$ subunit capable of associating with one another to form a complex capable of regulating the activity of the $\alpha$ subunit. More preferred G protein subunits of the present invention include $G_{12}$ and $G_{13}$. Even more preferred G protein subunits of the present invention include $G_{\alpha 12}$ and $G_{\alpha 13}$. As used herein, a G protein subunit can be referred to by the name of the subunit alone (e.g., $\alpha_{12}$ or $\alpha_{13}$) or by the full name $G_{\alpha 12}$ and $G_{\alpha 13}$. The name of the subunit and the full name of the G protein are used interchangeably and are intended to refer to the same molecule.

Particular G proteins are not useful when used in a method of the present invention. Specifically, preferred G proteins of the present invention do not include $\alpha_s, \alpha_{o1f}, \alpha_{i1}, \alpha_{i2}, \alpha_{i3}, \alpha_{o1,2}, \alpha_{t\ rod}, \alpha_{t\ cone}, \alpha_{gust}, \alpha_z, \alpha_q, \alpha_{11}, \alpha_{14}, \alpha_{15}, \alpha_{16}, \beta_1, \beta_2, \beta_3, \beta_4, \gamma_1, \gamma_2, \gamma_3, \gamma_4, \gamma_5, \gamma_6, \gamma_7, \gamma_8, \gamma_9$ and $\gamma_{10}$, $G\beta 2\gamma 2$ or $G\beta 1\gamma 2$.

Preferred low molecular weight G protein regulator molecules include regulator molecules of $p21^{ras}$, Rho and Rac. More preferred low molecular weight G protein regulator molecules include regulator molecules of Rho. Even more preferred low molecular weight G protein regulator molecules include a protein comprising a Dbl-homologous domain, a protein comprising a lbc-homologous domain, a Rho guanine nucleotide dissociation inhibitor and a Rho GTPase-activating protein. Yet even more preferred low molecular weight G protein regulator molecules include Dbl, Bcr, Vav, Ect2, Sos, RasGRF, RhoGDI, LyGDI, D4, RhoGAP, p190, 3BP-1, n-chimaerin, βchimaerin and p85.

A preferred low molecular weight G protein includes $p21^{ras}$, Rho or Rac. A more preferred low molecular weight G proteins includes Rho, with Rho A, Rho B and Rho C being even more preferred.

A preferred cell of the present invention has, amongst other signal transduction molecules, a G protein and/or a tyrosine kinase, and a Rho protein. A more preferred cell of the present invention has, amongst other signal transduction molecules, $G_{\alpha 12}$, $G_{\alpha 13}$ and Rho protein.

In a preferred embodiment, a cell of the present invention comprises: a C5aR, a Rantes receptor, an LPAR, a thrombin receptor, a GRPR, an IL-8R, a Substance P receptor, a vasopressin receptor and/or a bradykinin receptor; in addition to $G_{\alpha 12}$ protein, $G_{\alpha 13}$ protein, a Rho regulator molecule and Rho protein.

Signal transduction molecules referred to herein include the natural full-length protein, or can be a functionally equivalent protein in which amino acids have been deleted (e.g., a truncated version of the protein), inserted, inverted, substituted and/or derivatized (e.g., phosphorylated, acetylated, glycosylated, carboxymethylated, myristoylated, prenylated or palmitoylated amino acids) such that the modified protein has a biological activity and/or function substantially similar to that of the natural protein. Modifications can be accomplished by techniques known in the art, including, but not limited to, direct modifications to the protein or modifications to the gene encoding the protein. Such modifications to the gene encoding the protein can include using, for example, classic or recombinant DNA techniques to effect random or targeted mutagenesis (see, for example, Sambrook et al., *Molecular Cloning: A Laboratory Manual*, Cold Spring Harbor Labs Press, 1989, which is incorporated herein by reference in its entirety).

Functionally equivalent proteins can be selected using assays established to measure the biological activity of the protein. For example, a functionally equivalent cell surface receptor would have a similar ability to bind a particular ligand as would the corresponding natural cell surface receptor protein. As a further example, a functionally equivalent intracellular signal transduction protein would have a similar ability to associate with and regulate the activity of another intracellular molecule as would the corresponding natural intracellular signal transduction protein.

In certain embodiments, a cell of the present invention is transformed with at least one heterologous nucleic acid molecule. A nucleic acid molecule as described herein can be DNA, RNA, or hybrids or derivatives of either DNA or RNA. Nucleic acid molecules as referred to herein can include regulatory regions that control expression of the nucleic acid molecule (e.g., transcription or translation control regions), full-length or partial coding regions, and combinations thereof. It is to be understood that any portion of a nucleic acid molecule can be produced by: (1) isolating the molecule from its natural milieu; (2) using recombinant DNA technology (e.g., PCR amplification, cloning); or (3) using chemical synthesis methods. A gene includes all nucleic acid sequences related to a natural cell surface receptor gene such as regulatory regions that control production of a cell surface receptor encoded by that gene (such as, but not limited to, transcription, translation or post-translation control regions) as well as the coding region itself.

A nucleic acid molecule can include functional equivalents of natural nucleic acid molecules encoding a protein. Functional equivalents of natural nucleic acid molecules can include, but are not limited to, natural allelic variants and modified nucleic acid molecules in which nucleotides have been inserted, deleted, substituted, and/or inverted in such a manner that such modifications do not substantially interfere with the nucleic acid molecule's ability to encode a molecule of the present invention. Preferred functional equivalents include sequences capable of hybridizing under stringent conditions (i.e., sequences having at least about 70% identity), to at least a portion of a signal transduction protein encoding nucleic acid molecule according to conditions described in Sambrook et al., ibid.

As guidance in determining what particular modifications can be made to any particular nucleic acid molecule, one of skill in the art should consider several factors that, without the need for undue experimentation, permit a skilled artisan to appreciate workable embodiments of the present invention. For example, such factors include modifications to nucleic acid molecules done in a manner so as to maintain particular functional regions of the encoded proteins including, a ligand binding site, a target binding site, a nucleotide exchange domain, a kinase catalytic domain, etc. Functional tests for these various characteristics (e.g., ligand binding studies and signal transduction assays such as kinase assays, GTP binding assays, and other assays described in detail herein and those known by those in the art) allows one of skill in the art to determine what modifications to nucleic acid sequences would be appropriate and which would not.

Transformation of a heterologous nucleic acid molecule (e.g., a heterologous cell surface receptor encoding a nucleic acid molecule) into a cell suitable for use in the present invention can be accomplished by any method by which a gene is inserted into a cell. Transformation techniques include, but are not limited to, transfection, retroviral infection, electroporation, lipofection, bacterial transfer and spheroplast fusion. Nucleic acid molecules transformed into cells suitable for use in the present invention can either remain on extra-chromosomal vectors or can be integrated into the cell genome.

Expression of a nucleic acid molecule of the present invention in a cell can be accomplished using techniques known to those skilled in the art. Briefly, the nucleic acid molecule is inserted into an expression vector in such a manner that the nucleic acid molecule is operatively joined to a transcription control sequence in order to be capable of effecting either constitutive or regulated expression of the gene when the gene is transformed into a host cell. Construction of desired expression vectors can be performed by methods known to those skilled in the art and expression can be in eukaryotic or prokaryotic systems. An expression system can be constructed from control elements, including transcription control sequences, translation control sequences, origins of replication, and other regulatory sequences that are compatible with a host cell, operatively linked to nucleic acid sequences using methods known to those of skill in the art. (see, for example, Sambrook et al., ibid.).

In one embodiment, a cell suitable for use in the present invention is transformed with a nucleic acid molecule encoding at least one type of cell surface receptor, as described in detail herein. Preferred cell surface receptor-encoding nucleic acid molecules include, but are not limited to, nucleic acid molecules encoding G protein linked receptors and tyrosine kinase-coupled receptors. More preferred cell surface receptor encoding nucleic acid molecules include, but are not limited to, nucleic acid molecules encoding an LPAR, a thrombin receptor, a C5aR, an IL-8R, a MIP1αR, a MIP1βR, a MCP-1R, a MCP-3R, a PAFR, a FMLPR, a LTB$_4$R, a GRPR, a RANTES receptor, a Substance P receptor, a vasopressin receptor, a bradykinin receptor, an Abl-linked receptor, a BCR-ABL-linked receptor, a FcεRIβ, a FcγRI, a FcγRIII, a FcγRIIA, a FcαR, a TCR, a BCR. Even more preferred cell surface receptor-encoding nucleic acid molecules include, but are not limited to, nucleic acid molecules encoding a C5aR, a Rantes receptor, an LPAR, a thrombin receptor, an IL-8R, a GRPR, a Substance P receptor, a vasopressin receptor, a bradykinin receptor and mixture thereof.

In another embodiment of the present invention, a cell suitable for use in the present invention is transformed with a nucleic acid molecules encoding at least one type of intracellular signal transduction protein of the present invention. Preferred intracellular signal transduction protein encoding nucleic acid molecules include, but are not limited to, nucleic acid molecules encoding G proteins; kinases; low molecular weight G protein regulator molecules; and low molecular weight G proteins. More preferred intracellular signal transduction protein encoding nucleic acid molecules include, but are not limited to, nucleic acid molecules encoding $G_{\alpha12}$, $G_{\alpha13}$, p21$^{ras}$, Rho, Rac, MEKK, PAK kinases, Fyn, Lyn, Blk, Yes, Lck, Btk, Hck, Abl and BCR-Abl. Even more preferred intracellular signal transduction protein-encoding nucleic acid molecules include, but are not limited to, nucleic acid molecules encoding $G_{\alpha12}$, $G_{\alpha13}$, Rho, Fyn, Lyn, Blk, Yes, Lck, Btk, Hck, Abl, BCR-Abl and a Rho regulator molecule.

It is within the scope of the present invention that a cell can be transformed with both a nucleic acid molecule encoding at least one type of signal transduction molecule and a nucleic acid molecule encoding at least one type of cell surface receptor.

In one embodiment, the method of the present invention comprises contacting a cell with a putative regulatory compound. According to the present invention, putative regulatory compounds include compounds that are suspected of being capable of regulating actin polymerization, stress fiber formation and/or focal adhesion assembly. The term "activity" refers to any stage of activation of a signal transduction molecule by, for example, binding of a nucleotide, exchange of a nucleotide, conformational change of a molecule which results in the acquisition of catalytic activity by the molecule; the phosphorylation of a molecule, thereby resulting in the acquisition or loss of catalytic activity by the molecule; or the translocation of a molecule from one region of a cell to another, thereby enabling the molecule to bind another molecule. The term "regulate" refers to controlling the activity of a molecule and/or biological function, such as enhancing or diminishing such activity or function.

Putative compounds as referred to herein include, for example, compounds that are products of rational drug design, natural products and compounds having partially defined signal transduction regulatory properties. A putative compound can be a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof. A putative regulatory compound can be obtained, for example, from libraries of natural or synthetic compounds, in particular from chemical or combinatorial libraries (i.e., libraries of compounds that differ in sequence or size but that have the same building blocks; see for example, U.S. Pat. Nos. 5,010,175 and 5,266,684 of Rutter and Santi, which are incorporated herein by reference in their entirety) or by rational drug design.

In a rational drug design procedure, the three-dimensional structure of a compound, such as a signal transduction molecule can be analyzed by, for example, nuclear magnetic resonance (NMR) or x-ray crystallography. This three-dimensional structure can then be used to predict structures of potential compounds, such as putative regulatory compounds by, for example, computer modelling. The predicted compound structure can then be produced by, for example, chemical synthesis, recombinant DNA technology, or by isolating a mimetope from a natural source (e.g., plants, animals, bacteria and fungi). Potential regulatory compounds can also be identified using SELEX technology as described in, for example, PCT Publication Nos. WO 91/19813; WO 92/02536 and WO 93/03172 (which are incorporated herein by reference in their entirety).

In particular, a naturally-occurring intracellular signal transduction molecule can be modified based on an analysis of its structure and function to form a suitable regulatory compound. For example, a compound capable of regulating the activity of an a subunit of a G protein can comprise a compound having similar structure to a β or γ subunit (referred to herein as a β or γ subunit mimetope) of a G protein. As such, an α subunit regulatory compound can comprise at least a portion of a modified or unmodified β or γ subunit. Additionally, a compound capable of interfering with the association of a subunit of a G protein with a Rho regulator molecule can comprise a compound having similar structure to the Rho regulator molecule binding site (referred to herein as a Rho regulator mimetope) on the G protein subunit, or alternatively, a compound having similar structure to G protein subunit binding site (referred to herein as a G protein mimetope) on a Rho regulator molecule.

Also, de-regulated forms of intracellular signal transduction molecules having enzymatic or nucleotide exchange activity can be developed by analyzing the structure of the molecules. For example, de-regulated forms of a kinase can be formed by modifying the kinase by removing the amino terminus regulatory domain from the carboxy terminus kinase domain, thereby creating a constitutively active compound capable of regulating the activity of a Rho protein. Alternatively, de-regulated forms of a G protein can be formed by modifying the G protein by, for example, mutating a conserved glutamine (Q) adjacent to the G3 sequence of a GDP/GTP binding domain of the α chain of a G protein to a leucine (L). The Q to L mutation functionally inhibits the GTPase activity of the polypeptide resulting in a constitutively activated G protein α subunit. This mutation corresponds to residue 229 in $\alpha_{12}$ 226 in $\alpha_{13}$ (see, Example 1 below), thereby creating a constitutively active compound capable of regulating the activity of a Rho protein.

Putative regulatory compounds can also include molecules designed to interfere with receptors coupled to $G_{\alpha 12}$ and/or $G_{\alpha 13}$. For example, mutant receptors coupled to $G_{\alpha 12}$ and/or $G_{\alpha 13}$ can be created that interfere with the coupling of $G_{\alpha 12}$ and/or $G_{\alpha 13}$ with a receptor. Putative regulatory compounds can include agonists and antagonists of $G_{\alpha 12}$ and/or $G_{\alpha 13}$-coupled receptors. Such agonists and antagonists can be selected based on the structure of a naturally-occurring ligand to a G protein-coupled receptor.

The conditions under which the cell of the present invention is contacted with a putative regulatory compound, such as by mixing, are conditions in which the cell can form actin polymers, stress fibers and/or assemble focal adhesions if essentially no other regulatory compounds are present that would interfere with actin polymerization, stress fiber formation and/or focal adhesion assembly. Achieving such conditions is within the skill in the art, and includes an effective medium in which the cell can be cultured such that the cell can exhibit cytoskeletal rearrangement. For example, for a mammalian cell, effective media are typically aqueous media comprising Dulbecco's modified Eagle's medium containing 10% fetal calf serum.

Cells of the Cells of the present invention can be cultured in a variety of containers including, but not limited to, tissue culture flasks, test tubes, microtiter dishes, and petri plates. Culturing is carried out at a temperature, pH and carbon dioxide content appropriate for the cell. Such culturing conditions are also within the skill in the art. For example, for HELA cells, culturing can be carried out at 37° C., in a 5% $CO_2$ environment.

Acceptable protocols to contact a cell with a putative regulatory compound in an effective manner include the number of cells per container contacted, the concentration of putative regulatory compound(s) administered to a cell, the incubation time of the putative regulatory compound with the cell, the concentration of ligand and/or intracellular initiator molecules administered to a cell, and the incubation time of the ligand and/or intracellular initiator molecule with the cell. Determination of such protocols can be accomplished by those skilled in the art based on variables such as the size of the container, the volume of liquid in the container, the type of cell being tested and the chemical composition of the putative regulatory compound (i.e., size, charge etc.) being tested.

In one embodiment of the method of the present invention, a suitable number of cells are added to a 96-well tissue culture dish in culture medium. A preferred number of cells includes a number of cells that enables one to detect a change in cytoskeletal structure using a detection method of the present invention (described in detail below). A more preferred number of cells includes between about 1 and $1 \times 10^6$ cells per well of a 96-well tissue culture dish. Following addition of the cells to the tissue culture dish, the cells can be pre-incubated at 37° C., 5% $CO_2$ for between about 0 to about 24 hours.

A suitable amount of putative regulatory compound(s) suspended in culture medium is added to the cells that is sufficient to regulate the activity of a signal transduction molecule inside the cell such that the regulation is detectable using a detection method of the present invention. A preferred amount of putative regulatory compound(s) comprises between about 1 nM to about 10 mM of putative regulatory compound(s) per well of a 96-well plate. The cells are allowed to incubate for a suitable length of time to allow the putative regulatory compound to enter a cell and interact with a signal transduction molecule. A preferred incubation time is between about 1 minute to about 12 hours.

In another embodiment of the method of the present invention, cells suitable for use in the present invention are stimulated with stimulatory molecules capable of binding to cell surface receptors of the present invention to initiate a signal transduction pathway and create a cellular response. Preferably, cells are stimulated with a stimulatory molecule following contact of a putative regulatory compound with a cell. Suitable stimulatory molecules can include, for example, hormones, growth factors, antigens, peptides, ions, other differentiation agents and other cell type specific mitogens. Preferred stimulatory molecules include, but are not limited to, LPA, thrombin, C5a, IL-8, MIP1α, MIP1β, MCP-1, MCP-3, PAF, FMLP, $LTB_4$, GRP (including bombesin), RANTES, Substance P, vasopressin, bradykinin, IgE/antigen, IgG/antigen, IgA/antigen, and mixtures thereof. Particularly preferred stimulatory molecules of the present invention include, LPA, thrombin, C5a, IL-8, MCP-1, MIP1α, FMLP, RANTES, PAF, $LTB_4$, GRP (including bombesin), Substance P, vasopressin, bradykinin and mixtures thereof, with LPA, thrombin, IL-8, GRP (including bombesin) and a mixture thereof being even more preferred. A suitable amount of stimulatory molecule to add to a cell depends upon factors such as the type of ligand used (e.g., monomeric or multimeric; permeability, etc.) and the receptor being targeted (e.g., abundance of the receptor on a cell and the number of ligand binding sites/receptor). Preferably, between about 1.0 nM and about 1 mM of ligand is added to a cell.

In another embodiment of the present invention, cells suitable for use in the present invention are stimulated with intracellular initiator molecules capable of initiating actin polymerization, stress fiber formation and/or focal adhesion assembly from inside a cell. Examples of intracellular initiator molecules as referred to herein include, but are not limited to, Dbl, chaermein, Ibc, Rac, Rac exchange factors, Ras, Ras exchange factors, Rho and Rho exchange factors. A suitable amount of intracellular initiating molecules to add to a cell depends upon factors such as how efficiently the molecule can enter a cell and the concentration of the target molecule upon which the intracellular initiating molecule acts. Preferably, between about 1 nM and about 1 mM of intracellular initiating molecule is added to a cell.

The cells are allowed to incubate for a suitable length of time to allow the stimulatory molecule or intracellular initiator molecule to stimulate a signal transduction pathway. A preferred incubation time is between about 1 minute to about 24 hours.

The method of the present invention include determining if a putative regulatory compound is capable of regulating actin polymerization, stress fiber formation and/or focal adhesion assembly. Such methods include: guanosine triphosphate (GTP) binding assays (as generally described in Vaillancourt et al., ibid.); actin polymerization analysis; cellular analysis; and actin binding protein phosphorylation assays. The method of the present invention can further include the step of performing a toxicity test to determine the toxicity of a putative regulatory compound.

In one embodiment, the method of the present invention comprise detection of actin polymerization, stress fiber formation and/or focal adhesion assembly in a cell by determining the GTP binding and/or GTP exchange activity (using the methods of Vaillancourt et al., ibid.) of Rho protein. A preferred method comprises: (1) contacting a cell with a putative regulatory compound of the present invention; (2) stimulating the cell with a stimulatory molecule capable of inducing actin polymerization, stress fiber formation and/or focal adhesion assembly; and (3) measuring Rho GTP binding and/or exchange activity.

In another embodiment, the method of the present invention comprises detecting actin polymerization, stress fiber formation and/or focal adhesion assembly in a cell by determining alteration in a cell contacted with a putative regulatory compound, compared with a cell that has not been contacted with the same compound. For example, to measure the effectiveness of a putative regulatory compound for controlling actin polymerization, stress fiber formation and/or focal adhesion assembly one can observe the adhesiveness, growth, shape and motility characteristics of contacted and uncontacted cells. The extent of adhesiveness of a cell can be determined by whether a cell can be dislodged from a substratum by shaking or knocking the culture surface, or whether enzyme treatment, such as trypsin, is required to dislodge a cell from a substratum. Methods to dislodge cells from culture surfaces are well known in the art. Changes in cell growth can be determined by counting the number of live cells after a certain period of time (by, for example, coomassie blue staining), and/or by measuring the size of a cell after a certain period of time. Changes in cell shape can be determined by viewing cells to assess the flattening of cells on a substratum and/or the formation of cellular extensions, such as pseudopodium, filopodium and lamellipodium. Changes in cell motility can be determined by viewing the direction and distance a cell has traveled on a substratum during a certain period of time. Typically, such movement is associated with the formation of cellular extensions.

In another embodiment, the method of the present invention comprises detecting actin polymerization, stress fiber formation and/or focal adhesion assembly in a cell by determining changes in actin polymerization and/or organization. In such a method, the extent of actin polymerization and/or the organization of actin filaments are compared in cells contacted with a putative regulatory compound and cells not contacted with such a compound. The actin filaments are visualized by contacting the cells with labelled phalloidin (e.g., rhodamine conjugated phalloidin), which binds specifically to F-actin, using methods described herein (see, Example 1 below). Alternatively, actin filaments can be visualized using labelled antibodies that specifically bind to actin monomers or polymers, using methods known to those in the art. Additional methods include visualizing actin polymerization by electron microscopy.

In yet another embodiment, the method of the present invention comprises detecting actin polymerization, stress fiber formation and/or focal adhesion assembly in a cell by determining the phosphorylation of actin binding proteins including, but not limited to, focal adhesion kinase (FAK), paxillin and vinculin. Detection of phosphorylation include methods and reagents known to those of skill in the art, for example, phosphorylation can be detected using antibodies specific for phosphorylated amino acid residues. Alternatively, polymerized actin can be isolated by precipitation and the actin-associated proteins can be identified.

With respect to a separate embodiment of the present invention, a regulatory compound can be identified in a cell-free assay that includes the steps of: (1) contacting putative regulatory compound with a formulation comprising a Rho regulator molecule and a G protein capable of regulating the activity of the Rho regulator molecule; and (2) assessing the ability of the putative regulatory compound to regulate the activity of the Rho regulator molecule. Suitable G proteins and Rho regulator molecules for use with the present method include those described in detail herein. Preferably, the activity of a Rho regulator molecule is determined by stimulation of GTP binding to Rho (using methods described in Vaillancourt et al., ibid.) or increased actin polymerization.

Another embodiment of the present invention useful for identifying compounds capable of regulating actin polymerization, stress fiber formation and/or focal adhesion assembly includes a cell-based assay comprising: (1) contacting a cell with a putative regulatory compound, in which the cell includes a Rho protein and a first protein including a G protein or a tyrosine kinase; and (2) assessing the ability of the putative regulatory compound to regulate a biological function including actin polymerization, stress fiber formation and/or focal adhesion assembly in the cell by determining the ability of the first protein to regulate Rho protein activity in the cell. Suitable kinases of the present invention include tyrosine kinases. Preferred tyrosine kinases of the present invention are capable of regulating, directly or indirectly, the activity of a Rho regulator molecule. More preferred tyrosine kinases include src-family kinases, such as Fyn, Lyn, Blk, Yes, Lck, Btk, Hck, Src (including Abl and BCR-Abl). Preferably, Rho protein activity is determined by a method including determining guanine nucleotide binding to the Rho protein and/or guanine nucleotide exchange by the Rho protein, using methods described herein.

Another embodiment includes a cell-free assay comprising: (1) contacting a first protein including a G protein or a tyrosine kinase, and a second protein comprising a Rho regulator molecule, with a putative regulatory compound; and (2) assessing the ability of the putative regulatory compound to regulate the activity of the Rho regulator molecule by determining the activity of the Rho regulator molecule. Rho regulator activity is preferably determined using methods described herein.

Another aspect of the present invention includes a kit to identify compounds capable of regulating actin polymerization, stress fiber formation and/or focal adhesion assembly in a cell, such biological functions involving in some respect, $G_{\alpha 12}$ and/or $G_{\alpha 13}$ protein. Such a kit includes: (1) a cell comprising a Rho protein and a protein including a G protein or a tyrosine kinase; and (2) a means for detecting regulation of the Rho protein. Such a means for detecting the regulation of Rho protein include methods and reagents known to those of skill in the art, for example, GTP binding to Rho protein can be detected using GTP binding assays described in detail herein. Suitable cells for use with a kit of the present invention include cells described in detail herein. A preferred cell for use with a kit includes, a mammalian cell, an amphibian cell and a yeast cell.

The present invention also includes the determination as to whether a putative regulatory compound is capable of regulating a biological response in a mammal. Such a method entails administering a putative regulatory compound to an animal, such compound being shown, using an assay of the present invention, to regulate actin polymerization, stress fiber formation and/or focal adhesion assembly in a cell. Such a determination is useful for determining conditions under which a putative regulatory compound can be administered to an animal as a therapeutic composition. Thus, it is within the scope of the present invention that those conditions stated herein for testing a compound in an animal can be used when administering a therapeutic composition of the present invention. In particular, a putative regulatory compound can be administered to an animal to determine if the compound is capable of regulating, for example, an inflammatory response, a response to an infectious agent, an autoimmune response, a metabolic response, a cardiovascular response, an allergic response and/or an abnormal cellular growth response in the animal. Acceptable protocols to administer putative regulatory compounds to test the effectiveness of the compound include individual dose size, number of doses, frequency of dose administration, and mode of administration. Determination of such protocols can be accomplished by those skilled in the art. A suitable single dose is a dose that is capable of altering a biological response in an animal when administered one or more times over a suitable time period (e.g., from minutes to days or weeks). Preferably, a dose comprises from about 1 nanogram of the compound per kilogram of body weight (ng/kg) to about 1 gram of compound per kilogram of body weight (gm/kg), more preferably 100 ng/kg to about 100 milligrams/kilogram (mg/kg), and even more preferably from about 10 micrograms of compound per kilogram of body weight to about 10 mg/kg. Modes of administration can include, but are not limited to, subcutaneous, rectally, intradermal, intravenous, nasal, oral, transdermal and intramuscular routes. A putative regulatory compound can be combined with other components such as a pharmaceutically acceptable excipient and/or a carrier, prior to administration to an animal. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Carriers are typically compounds that increase the half-life of a compound in the treated animal. Suitable carriers include, but are not limited to, polymeric controlled release vehicles, biodegradable implants, liposomes, bacteria, viruses, oils, esters, and glycols. Preferred controlled release formulations are capable of slowly releasing a composition of the present invention into an animal. Suitable controlled release vehicles include, but are not limited to, biocompatible polymers, other polymeric matrices, capsules, microcapsules, microparticles, bolus preparations, osmotic pumps, diffusion devices, liposomes, liposheres, and transdermal delivery systems. Other controlled release vehicles of the present invention include liquids that, upon administration to an animal, form a solid or a gel in situ. Preferred controlled release vehicles are biodegradable (i.e., bioerodible).

In another aspect of the present invention, the present invention includes conducting a toxicity test on an animal to determine the toxicity of a putative regulatory compound. Toxicity tests for putative regulatory compounds can be performed, for example, on animals after a putative regulatory compound has been determined to have an effect at the cellular level on signal transduction, such as the regulation of cellular inflammatory responses. Such toxicity tests are within the skill of the art, and generally involve testing the toxicity of a compound in vivo or in vitro. A suitable method for testing the toxicity of a putative regulatory compound in vivo can involve scientifically controlled administration of the putative regulatory compound to a number of animals and a period of observance in which the effects of the compound on various aspects of the animal's biological functions (e.g., occurrence of tissue damage, functioning of organs and death) are noted. Suitable methods for testing the toxicity of a putative regulatory compound in vitro can involve scientifically controlled administration of the putative regulatory compound to a cell and subsequent measurement of cell function, cytotoxicity, or cell death. Cell function can be measured by any one of a wide range of assays which will be apparent to one of skill in the art, several of which are herein disclosed (e.g., tyrosine phosphorylation, calcium mobilization and phosphoinositide assays). Methods to measure cytotoxicity are well known in the art and include measurement of the ability to reduce chromogenic substrates such as the tetrazolium-based MTT or sulphorhodamine blue, ATP-bioluminescence assays and fluorescence assays, for example using the Fluorescent Green Protein, among many other readily available assays (see, for example, Bellamy, Drugs 44(5):690–708, 1992, which is incorporated herein by reference in its entirety). Methods to measure cell death include, for example, Coomassie blue staining, acridine orange staining, terminal deoxynucelotidyl transferase (TDT) assays for measuring DNA fragmentation, neutral red exclusion, and measuring changes in forward light scattering in a flow cytometer.

Another aspect of the present invention includes a method to regulate actin polymerization, stress fiber formation and/or focal adhesion assembly, comprising regulating the activity of a protein including $G_{\alpha 12}$ and/or $G_{\alpha 13}$. In particular, the present invention includes a method to regulate cell chemotaxis by regulating the activity of a protein including $G_{\alpha 12}$ and/or $G_{\alpha 13}$. As used herein, the term "chemotaxis" refers to the attraction of a cell by a specific chemical. For example, a leukocyte undergoes chemotaxis to the site of a wound by being attracted by chemicals released by damaged cells.

Regulation of the activity of $G_{\alpha 12}$ and/or $G_{\alpha 13}$ includes regulating the activity of a Rho-dependent pathway (i.e., a signal transduction pathway having one signal transduction molecule being Rho protein) by sequestering a $G_{\alpha 12}$ and/or a $G_{\alpha 13}$ protein in an inactive complex, regulating the nucleotide exchange region of a $G_{\alpha 12}$ and/or a $G_{\alpha 13}$ protein, regulating GTP hydrolysis by a $G_{\alpha 12}$ and/or a $G_{\alpha 13}$ protein, regulating a cell surface receptor interaction with a $G_{\alpha 12}$ and/or a $G_{\alpha 13}$ protein, regulating the interaction between a $G_{\alpha 12}$ and/or a $G_{\alpha 13}$ protein with a Rho regulator molecule, regulating the expression of endogenous and/or heterologous nucleic acid molecules encoding a $G_{\alpha 12}$ and/or a $G_{\alpha 13}$ protein, and combinations thereof.

Suitable compounds for sequestering a $G_{\alpha 12}$ and/or a $G_{\alpha 13}$ protein in an inactive complex, include receptor antagonists at the extracellular ligand binding site, allosteric regulators of $G_{\alpha 12}$ and/or $G_{\alpha 13}$-coupled receptors, compounds that inhibit receptor coupling to $G_{\alpha 12}$ and/or $G_{\alpha 13}$, compounds that inhibit GTP binding to $G_{\alpha 12}$ and/or $G_{\alpha 13}$ or compounds that inhibit binding of $G_{\alpha 12}$ and/or $G_{\alpha 13}$ to Rho regulatory molecules.

Suitable compounds for regulating the nucleotide exchange region of a $G_{\alpha 12}$ and/or a $G_{\alpha 13}$ protein, include nucleotide analogs.

Suitable compounds for regulating a cell surface receptor interaction with a $G_{\alpha 12}$ and/or a $G_{\alpha 13}$ protein, include antagonists or reverse agonists of extracellular ligands to G protein-coupled receptors.

Suitable methods for regulating the expression of endogenous and/or heterologous nucleic acid molecules encoding a $G_{\alpha 12}$ and/or a $G_{\alpha 13}$ protein include methods known to those in the art. For example, oligonucleotides for use in, for example, antisense-, triplex formation-, ribozyme- and/or RNA drug-based technologies can be used to reduce expression of endogenous nucleic acid molecules encoding a $G_{\alpha 12}$ and/or a $G_{\alpha 13}$ protein. The present invention, therefore, includes such oligonucleotides and methods to interfere with the production of $G_{\alpha 12}$ and/or a $G_{\alpha 13}$ proteins by use of one or more of such technologies. Alternatively, a cell can be transformed with a nucleic acid molecule encoding $G_{\alpha 12}$ and/or a $G_{\alpha 13}$ protein to increase expression of $G_{\alpha 12}$ and/or a $G_{\alpha 13}$ protein. Appropriate expression vectors can be developed by those skilled in the art based upon the cell-type being transformed.

Another aspect of the present invention comprises administering to an animal, a therapeutic composition capable of regulating actin polymerization, stress fiber formation and/or focal adhesion assembly. A therapeutic composition of the present invention is particularly useful for preventing or treating diseases involving abnormal growth or the migration of cells from one location in an animal to another. In particular, a therapeutic composition is useful for preventing or treating diseases involving an inflammatory response, an immune response, an allergic response, a neuronal response, an apoptotic response, tumorigenesis, angiogenesis, metastases, hyperplasia or restenosis. Preferably, a therapeutic composition of the present invention is used to prevent or treat a disease, including, but not limited to, cancer, respiratory distress syndrome, inflammatory bowel disease, Parkinson's disease, Alzheimer's disease or restenosis. A therapeutic composition is preferably administered to a cell, including, but not limited to, a smooth muscle cell, an endothelial cell, an epithelial cell, a basophil, a mast cell, an eosinophil, a neutrophil, a macrophage, a B lymphocyte, a T lymphocyte, a dendritic cell, a natural killer cell, a plasma cell, a neuroblast, a stem cell or a cancer cell. A therapeutic composition is more preferably administered to a cell, including, but not limited to, a small cell lung carcinoma, a non-small cell lung carcinoma comprising overexpressed epidermal growth factor (EGF) receptors (i.e., having more EGF receptors than the number normally found on non-cancer lung cells), a breast cancer cell comprising overexpressed EGF receptors (i.e., having more EGF receptors than the number normally found on mammary cells), a breast cancer cell comprising overexpressed Neu receptors (i.e., having more Neu receptors than the number normally found on mammary cells), a cancer cell comprising an overexpressed growth factor receptor of an established autocrine loop (i.e., having more growth factor receptors than the number normally found on non-cancer cells) or a cancer cell comprising an overexpressed growth factor receptor of an established paracrine loop (i.e., having more growth factor receptors than the number normally found on non-cancer cells).

A variety of therapeutic compositions can be used to perform the regulation method of the present invention. Such therapeutic compositions include those compounds described in detail herein, in particular, compounds identified using a method of the present invention. A therapeutic composition of the present invention can be formulated in an excipient that the animal to be treated can tolerate. Examples of such excipients include those described in detail above. In order to regulate the formation of actin polymerization, stress fibers and/or the assembly of focal adhesions in a cell, a therapeutic composition of the present invention can be administered in vivo (i.e., in an animal) or ex vivo (i.e., outside of an animal, such as in tissue culture), in an effective manner such that the composition is capable of regulating actin polymerization, stress fiber formation and/or focal adhesion assembly.

An effective administration protocol (i.e., administering a therapeutic composition in an effective manner) comprises suitable dose parameters and modes of administration that result in prevention or treatment of a disease. Effective dose parameters and modes of administration can be determined using methods standard in the art for a particular disease. Such methods include, for example, determination of survival rates, side effects (i.e., toxicity) and progression or regression of disease. For example, the effectiveness of dose parameters and modes of administration of a therapeutic composition of the present invention can be determined by assessing response rates. Such response rates refer to the percentage of treated patients in a population of patients that respond with either partial or complete remission.

In accordance with the present invention, a suitable single dose size is a dose that is capable of preventing or treating an animal with a disease when administered one or more times over a suitable time period. Doses can vary depending upon the disease being treated. For example, in the treatment of cancer, a suitable single dose can be dependent upon whether the cancer being treated is a primary tumor or a metastatic form of cancer.

It will be obvious to one of skill in the art that the number of doses administered to an animal is dependent upon the extent of the disease and the response of an individual patient to the treatment. For example, in the case of cancer, a large tumor may require more doses than a smaller tumor. In some cases, however, a patient having a large tumor may require fewer doses than a patient with a smaller tumor, if the patient with the large tumor responds more favorably to the therapeutic composition than the patient with the smaller tumor. Thus, it is within the scope of the present invention that a suitable number of doses, as well as the time periods between administration, includes any number required to cause regression of a disease.

Therapeutic compositions can be administered directly to a cell in vivo or ex vivo or systemically. Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., *Proc. Natl. Acad. Sci. USA* 189:11277–11281, 1992, which is incorporated herein by reference in its entirety). Oral delivery can be performed by complexing a therapeutic composition of the present invention to a carrier capable of withstanding degradation by digestive enzymes in the gut of an animal. Examples of such carriers, include plastic capsules or tablets, such as those known in the art. Topical delivery can be performed by mixing a therapeutic composition of the present invention with a lipophilic reagent (e.g., DMSO) that is capable of passing into the skin.

The following examples are provided for the purposes of illustration and are not intended to limit the scope of the present invention.

EXAMPLES

Example 1

This example describes the stimulation of actin polymerization, stress fiber formation and focal adhesion assembly in cells transformed with GTPase-deficient mutants of Rho A, $G_{\alpha 12}$ and $G_{\alpha 13}$.

A. Preparation of GTPase-deficient mutants of Rho A, $G_{\alpha 12}$ and $G_{\alpha 13}$.

Initially, a cDNA clone encoding a mutant a subunit of $G_{12}$ was prepared by point mutation according to methods described by Promega (Madison, Wis.) and ligated into the expression vector pCDNA3 (obtained from InVitrogen, San Diego, Calif.) to form the expression plasmid pCNDA3$\alpha_{12}$QL. The oligonucleotides used for mutagenesis were synthesized using an Applied Biosystems Nucleotide Synthesizer (Applied Biosystems, Foster City, Calif.). The α chain was altered by mutating a conserved glutamine (Q) at residue 229 in $\alpha_{12}$, adjacent to the G3 sequence of a GDP/GTP binding domain of the α chain of a $G_{12}$ protein, to a leucine (L) (the Q to L mutation is referred to herein as Q→L) by point mutation as described above. The Q→L mutation functionally inhibits the GTPase activity of the polypeptide resulting in a constitutively activated G protein α subunit, thereby creating a constitutively active compound.

Similarly, a cDNA clone encoding a mutant a subunit of $G_{13}$ was prepared by point mutation and ligated into the expression vector pCDNA3 (obtained from InVitrogen) to form the expression plasmid pCNDA3$\alpha_{13}$QL. The a chain of a $G_{13}$ protein was altered by point mutation (Promega) of a conserved glutamine (Q) at residue 226 in $\alpha_{13}$.

A cDNA clone encoding a mutant Rho A protein was altered by mutating a conserved glutamine (Q) at residue 63 mutated to leucine (RhoQL) by point mutation (Promega) and ligated into the expression vector pCMV (obtained from David Russell, University of Texas, Southwestern) to form the expression plasmid pCMVRhoQL. The Q→L mutation functionally inhibits the GTPase activity of the polypeptide resulting in a constitutively activated Rho A protein, thereby creating acconstitutively active compound.

The expression plasmid pCMVβgal was obtained from InVitrogen.

All expression plasmids were prepared for microinjection by cesium chloride gradient centrifugation.

B. Microinjection of Cells with Expression Plasmids
Swiss 3T3 cells were prepared for microinjection with DNA plasmids as follows. Swiss 3T3 cells were plated at approximately 10% confluency on acid-washed glass coverslips in Dulbecco's Modified Eagles' Medium (DMEM) with 5% bovine calf serum (BCS) and 5% Newborn calf serum (NCS). The next day cells were rinsed three times and placed in 0.1% BCS/DMEM. Twenty-four hr later cells were rinsed three times in DMEM in the absence of serum and incubated for an additional 18 hr before microinjection.

Microinjections were performed using an Eppendorf automated microinjection system with needles pulled from glass capillaries on a vertical pipet puller (Kopf, Tujunga, Calif.). The nuclei of the Swiss 3T3 cells were injected with about 100 ng/μl of pCMVβgal and pCMVRhoQL; pCMVβgal and pCNDA3$\alpha_{12}$QL; or pCMVβgal and pCNDA3$\alpha_{13}$QL plasmid. expression plasmid. Successfully microinjected cells were detected by indirect immunofluorescent staining of β-galactosidase using a rabbit anti-β-galactosidase antibody (Cappel, Calif.) and a secondary FITC-conjugated donkey anti-rabbit antibody (Pierce, St. Louis, Mo.) using methods standard in the art. Cells successfully injected with pCNDA3$\alpha_{12}$QL or pCNDA3$\alpha_{13}$QL were detected by immunostaining injected cells with antisera specific for a peptide comprising a 12 amino acid portion of the C-terminal of $\alpha_{12}$ or $\alpha_{13}$ using methods standard in the art.

C. Actin Polymerization, Stress Fiber Formation and Focal Adhesion Assembly in Cells Expressing Constitutively Active Rho A protein, $G_{\alpha 12}$ or $G_{\alpha 13}$ Protein.

Two-to-three hr post-nuclear injection, cells were fixed in 3% paraformaldehyde for 10 min. Cells were rinsed in phosphate buffered saline and permeabilized using 0.2% Triton X-100 for 5 min. The fixed and permeabilized cells were then incubated with DMEM/5%, BCS/5% NCS for 15 min. Expression of microinjected expression plasmid was confirmed by immunostaining permeabilized cells for the presence of β-galactosidase protein using the method described above. Stress fiber formation in injected cells was detected by incubating the permeabilized cells in about 0.2 units/milliliter of Rhodamine-phalloidin (Molecular Probes, Eugene, Oreg.) for about 30 minutes at 24° C. Focal adhesion assembly in injected cells was detected by immunostaining permeabilized cells with a mouse monoclonal anti-vinculin antibody (Sigma, St. Louis, Mo.) and a secondary FITC-conjugated sheep anti-mouse (Cappel) antibody using methods standard in the art. Focal adhesion assembly is represented by the localization of vinculin staining at the leading edge of cells. When cells were stained for vinculin a rhodamine-conjugated goat anti-rabbit antibody (Cappel) was used for detection of β-galactosidase. Coverslips were mounted on slides and examined with a Nikon Diaphot TMD microscope with eipfluorescence. Images of cells were captured using the IPLAB Spectrum digital image analysis program (Signal Analytics Co., Vienna, Va.). All experiments were done at least 3–4 times with similar results.

Figure 1:
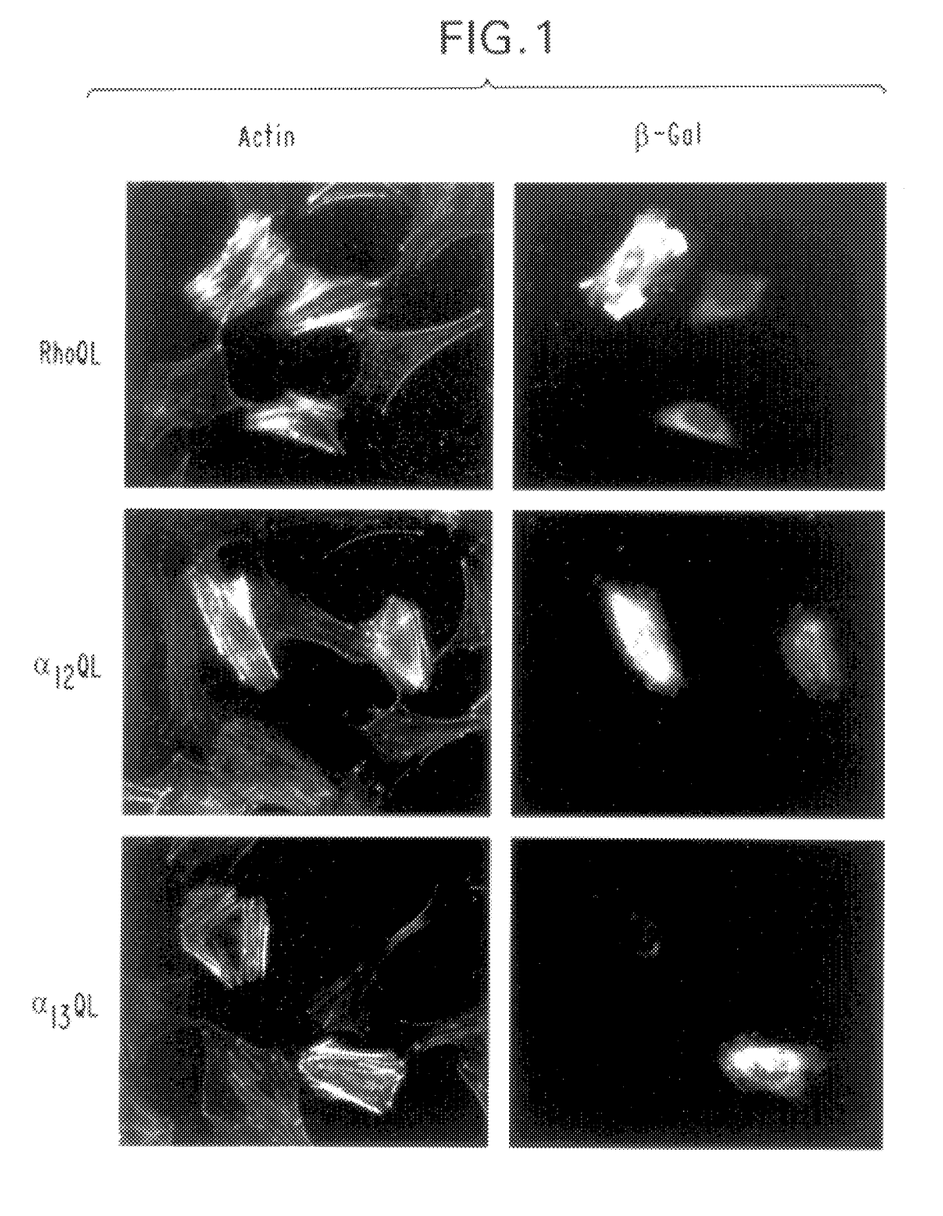
FIG. 1 illustrates stress fiber formation in Swiss 3T3 cells microinjected with expression plasmids encoding constitutively activated Rho, $G_{\alpha 12}$ and $G_{\alpha 13}$ protein.

The effects of expression of pCMVRhoQL, pCNDA3$\alpha_{12}$QL, or pCNDA3$\alpha_{13}$QL on stress fiber formation are shown in FIG. 1. The results from Rhodamine-phalloidin labeling of F-actin indicates that Rho A protein, having glutamine 63 mutated to leucine induces, stress fiber formation in Swiss 3T3 cells. In addition, the Q→L mutant of a subunits for $G_{12}$ ($\alpha_{12}$QL) and $G_{13}$ ($\alpha_{13}$QL) when expressed in Swiss 3T3 cells mimicked activated RhoQL in stimulating the formation of stress fibers. Uninjected cells in the field of view, that are negative for β-galactosidase staining, show few stress fibers.

Figure 2:
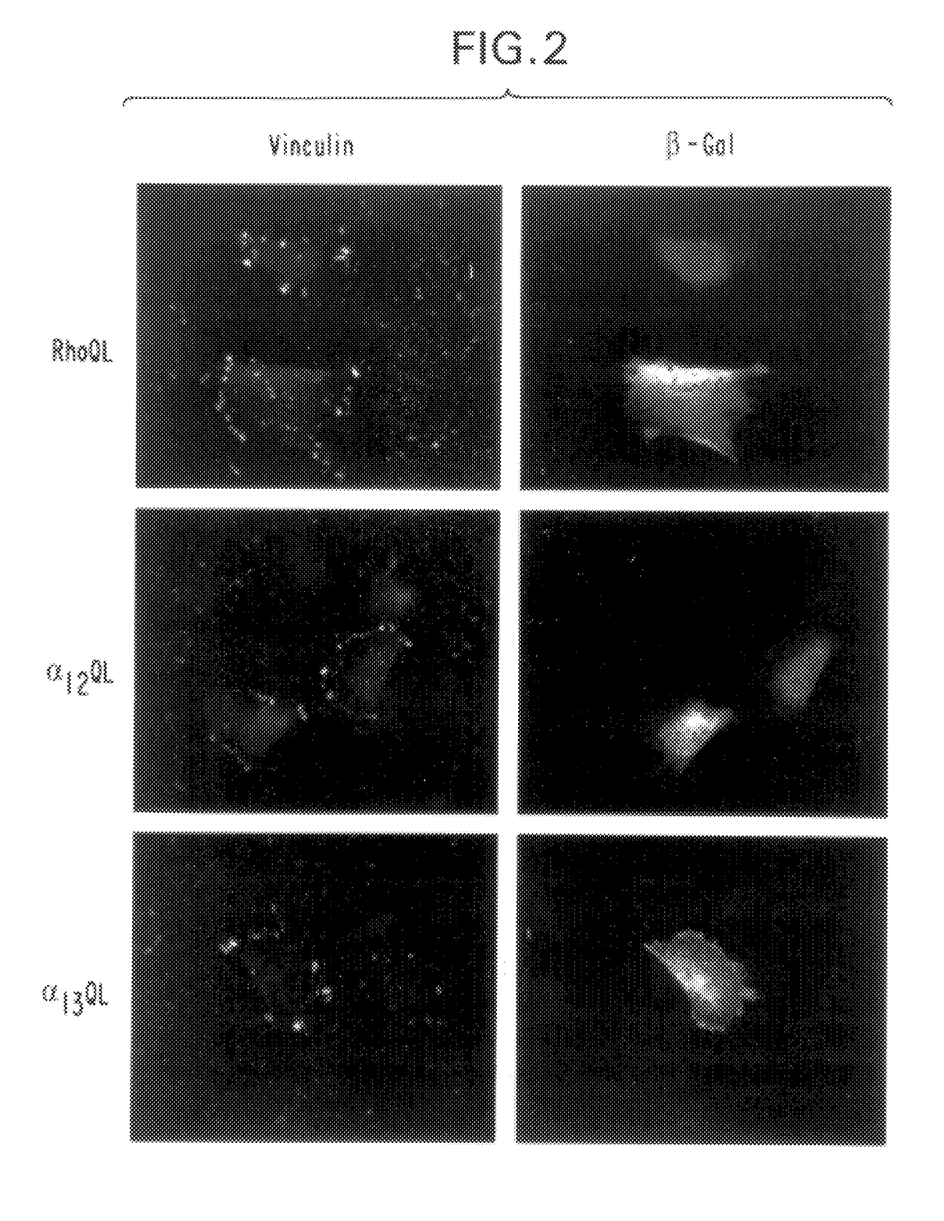
FIG. 2 illustrates focal adhesion assembly in Swiss 3T3 cells microinjected with expression plasmids encoding constitutively activated Rho, $G_{\alpha 12}$ and $G_{\alpha 13}$ protein.

The effects of expression of pCMVRhoQL, pCNDA3$\alpha_{12}$QL, or pCNDA3$\alpha_{13}$QL on focal adhesion assembly are shown in FIG. 2. The results of staining with antibodies specific for vinculin indicate that expression of RhoQL in quiescent Swiss 3T3 cells stimulates focal adhesion assembly. In addition, microinjection and expression of $\alpha_{12}$QL and $\alpha_3$QL mimicked RhoQL in stimulating focal adhesion assembly. Thus, activated forms of $\alpha_{12}$ and $\alpha_{13}$ regulate the polymerization of actin and the assembly of focal adhesions similar to that observed with RhoQL.

Example 2

This example describes that activated, GTPase deficient forms of $G_{\alpha i2}$ or $G_{\alpha q}$ are unable to induce stress fiber formation.

A. Preparation of Expression Plasmids Encoding $\alpha_{12}$QL, $\alpha_q$QL, β1γ2 or γ2γ2 subunits of G proteins.

cDNA clones encoding mutant forms of $\alpha_{i2}$QL, $\alpha_q$QL, β1 and γ2 or β2 and γ2 subunits of G proteins were prepared as described in Johnson et al. (J. Cell. Biochem. 47:136–146, 1991). $G_{\alpha i2}$ was altered by mutating a conserved glutamine (Q) at residue 205 mutated to leucine ($\alpha_{i2}$QL) and cloned into pCMV5 to form the expression plasmid pCMV$\alpha_{i2}$QL.

$G_{\alpha q}$ was altered by mutating a conserved glutamine (Q) at residue 209 mutated to leucine ($\alpha_q$QL) and cloned into pCMV5 to form the expression plasmid pCMVα$_q$QL as described in Qian et al. (*Proc. Natl. Acad. Sci. USA* 90:4077–4081, 1993).

CDNA clones encoding Gβ1γ2 and Gβ2γ2 each were cloned into pCMV5 to form the expression plasmid pCMVβ1γ2 and pCMVβ2γ2, respectively.

All expression plasmids were prepared for microinjection by cesium chloride gradient centrifugation.

Swiss 3T3 cells were prepared and nuclear microinjected as described in Example 1 with pCMVβgal and pCNDA3α$_{13}$QL, pCMVα$_{i2}$QL, pCMVα$_q$QL, pCMVβ1γ2 or pCMVβ2γ2. Microinjected cells were detected by staining for β-galactosidase as described in Example 1.

Figure 3:
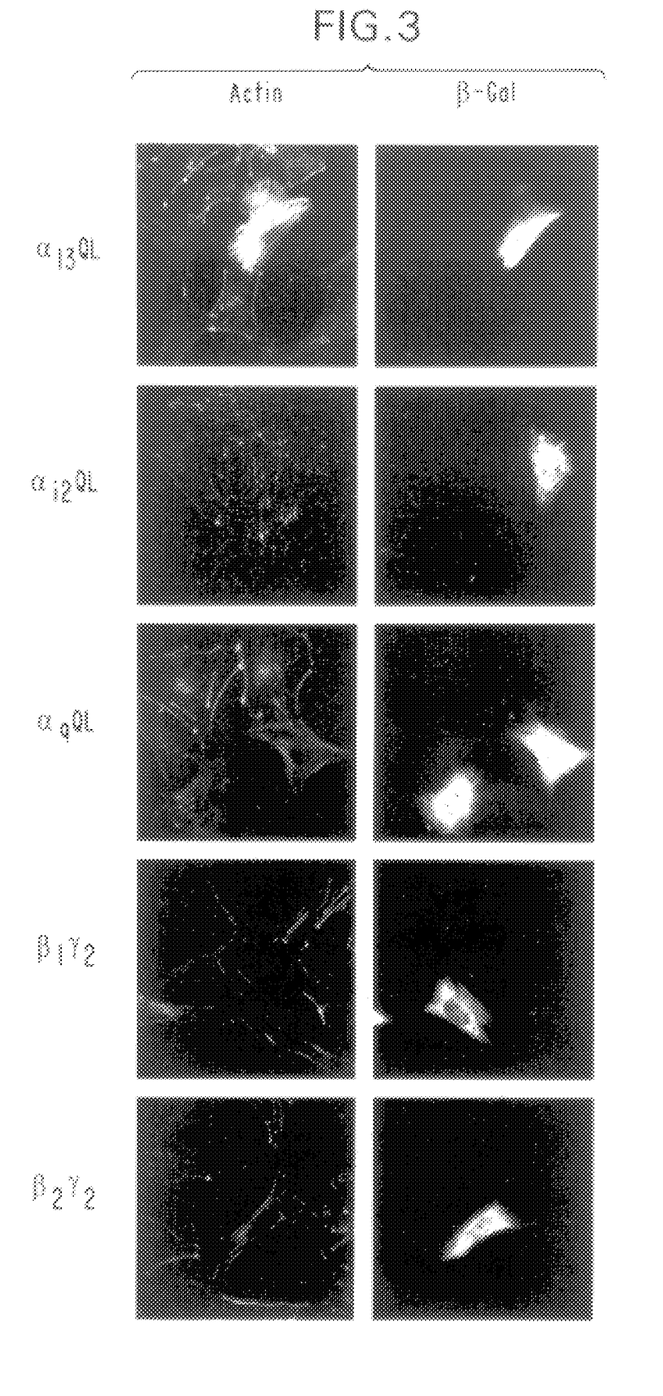
FIG. 3 illustrates the absence of stress fiber formation in Swiss 3T3 cells microinjected with expression plasmids encoding constitutively activated $G_{\alpha 13}$, $G_{\alpha 12}$, $G_{\alpha q}$, $G_{\beta 1\gamma 2}$ and $G_{\beta 2\gamma 2}$ protein.

Microinjected cells were permeabilized and stained with anti-β-galactosidase and labeled with Rhodamine-phalloidin as described in Example 1. The effects of expression of pCNDA3α$_{13}$QL, pCMVα$_{i2}$QL, pCMVα$_q$QL, pCMVβ1γ2 or pCMVβ2γ2 on stress fiber formation are shown in FIG. 3. The results from Rhodamine-phalloidin labeling of F-actin indicates that activated, GTPase deficient forms of α$_{i2}$ (α$_{i2}$QL) or α$_{q\;(\alpha q}$QL) were unable to induce stress fiber formation. Expression of α$_q$QL appears to disorder stress fibers and cause a loss of cortical actin along the cytoplasmic surface of the plasma membrane. Expression of β1γ2 or β1γ2 also did not induce stress fiber formation in Swiss 3T3 cells.

Example 3

This example describes the regulation of Rho protein activity by G$_{\alpha12}$QL and G$_{\alpha13}$QL were Rho-dependent.

A. Botulinum C3 Exoenzyme is an Effective Reagent for Stimulating Rho-dependent Stress Fiber Formation.

Recombinant, purified botulinum C3 exoenzyme was prepared using the following protocol. Botulinum C3 exoenzyme is capable of inhibiting Rho activity by catalyzing the ADP-ribosylation of Asn41 in Rho protein. A cDNA encoding botulinum C3 exoenzyme contained in a pGEX2T vector was used prepared as described in Dillon et al. (*Methods Enzymol.* 256:174–184, 1995). Botulinum C3 exoenzyme fusion protein was produced using the induction, thrombin cleavage and purification methods described in Dillon et al. (ibid.).

Swiss 3T3 cells were prepared and microinjected using the methods described in Example 1, with pCMVβgal and purified botulinum C3 exoenzyme (100 ng/μl). After 2–3 hrs, the injected cells were stimulated for 10 min with either lysophosphatidic acid (LPA; 200 ng/ml) which demonstrates Rho-File dependent stress fiber formation, platelet derived growth factor (PDGF; 3 ng/ml) which demonstrates Rho-independent stress fiber formation, or buffer only (Control). The stimulated cells were then fixed and immunostained for the presence of β-galactosidase using the methods described in Example 1.

Figure 4:
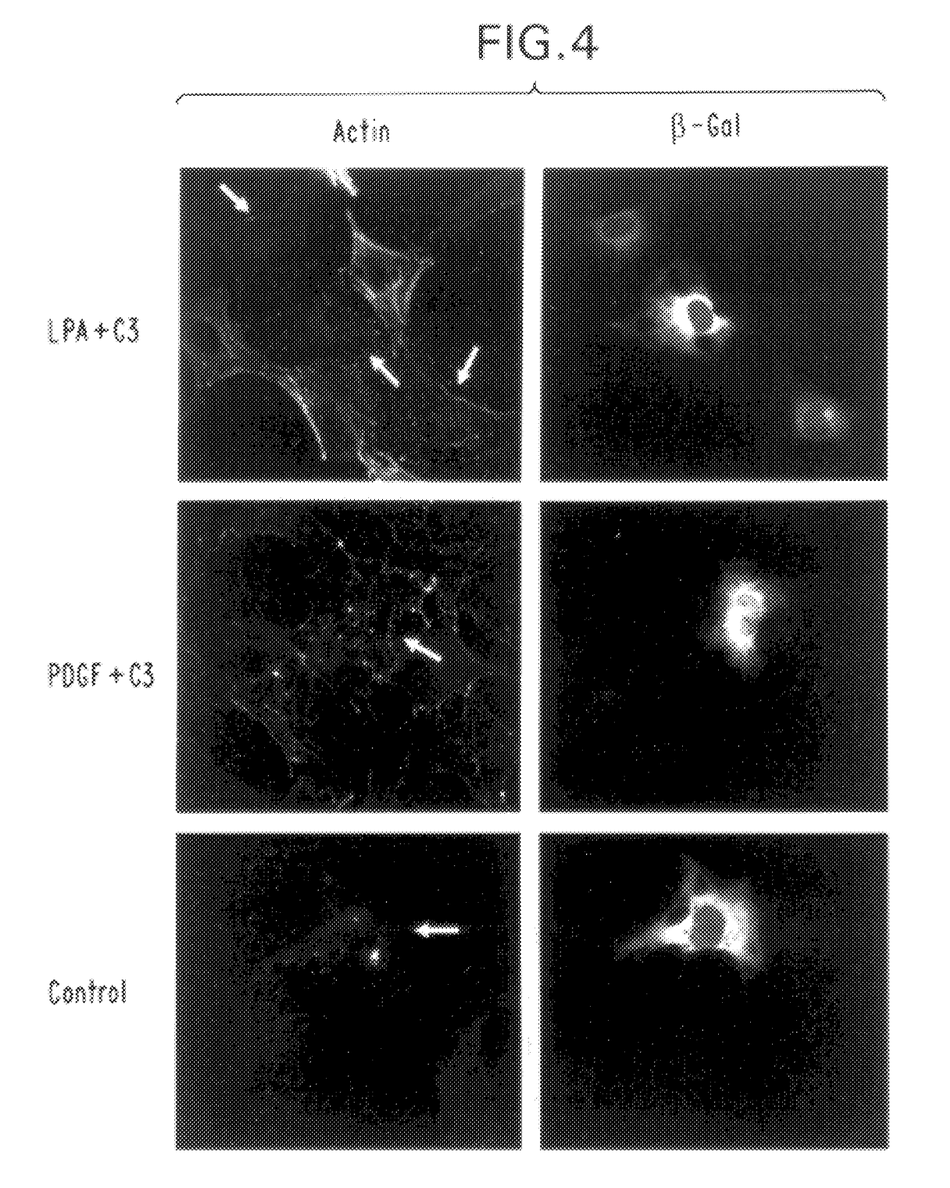
FIG. 4 illustrates stress fiber formation in Swiss 3T3 cells microinjected with botulinum C3 exoenzyme and stimulated with LPA or PDGF.

The microinjected cells treated with LPA or PDGF, or control cells were then fixed, permeabilized and labeled with Rhodamine-phalloidin or anti-β-galactosidase antibody using the methods described in Example 1. The effect of microinjection of botulinum C3 exoenzyme on stress fiber formation is shown in FIG. 4. The results indicate that microinjection of botulinum C3 exoenzyme inhibits LPA-stimulated stress fiber formation. LPA stimulated stress fiber formation is observed in control cells.

PDGF is capable of stimulating Rac 1-dependent actin polymerization that is associated with membrane ruffling. PDGF-stimulated membrane ruffling was unaffected in the botulinum C3 exoenzyme injected cells.

Thus, botulinum C3 exoenzyme is an effective reagent for stimulating Rho-dependent stress fiber formation.

B. Botulinum C3 Exoenzyme Inhibits Activated α$_{12}$ and α$_{13}$-Stimulated Stress Fiber Formation and focal adhesion assembly.

Swiss 3T3 cells were prepared and nuclear microinjected with pCMVβ-gal, and pCNDA3α$_{12}$QL or pCNDA3α$_{13}$QL as described in Example 1, in the presence or absence of botulinum C3 exoenzyme (100 ng/μl). Microinjected cells were detected by staining for β-galactosidase also as described in Example 1.

Figure 5:
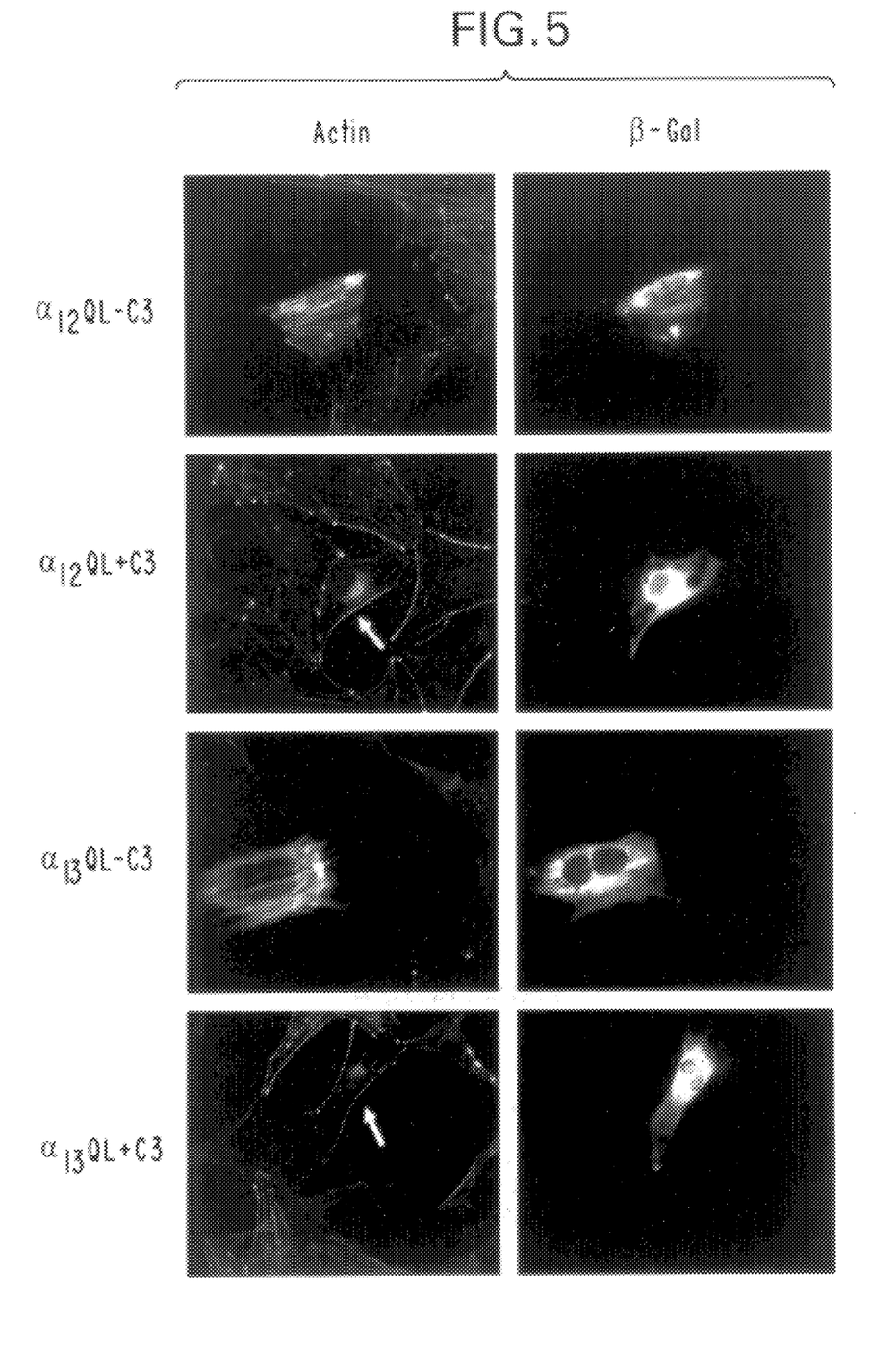
FIG. 5 illustrates stress fiber formation in Swiss 3T3 cells microinjected with an expression plasmid encoding constitutively activated $G_{\alpha 12}$ or $G_{\alpha 13}$ protein, in the presence or absence of botulinum C3 exoenzyme.

To determine the effect of botulinum C3 exoenzyme on stress fiber formation, samples of microinjected cells were fixed, permeabilized and labeled with Rhodamine-phalloidin and anti-β-galactosidase antibody using the methods described in Example 1. The effects of microinjection of botulinum C3 exoenzyme, and α$_{12}$QL or α$_{13}$QL on stress fiber formation are shown in FIG. 5. The results indicate that microinjection of botulinum C3 exoenzyme inhibited both α$_{12}$QL and α$_{13}$QL stimulated stress fiber formation similar to the inhibition of LPA-stimulated actin polymerization (as shown in FIG. 4).

Figure 6:
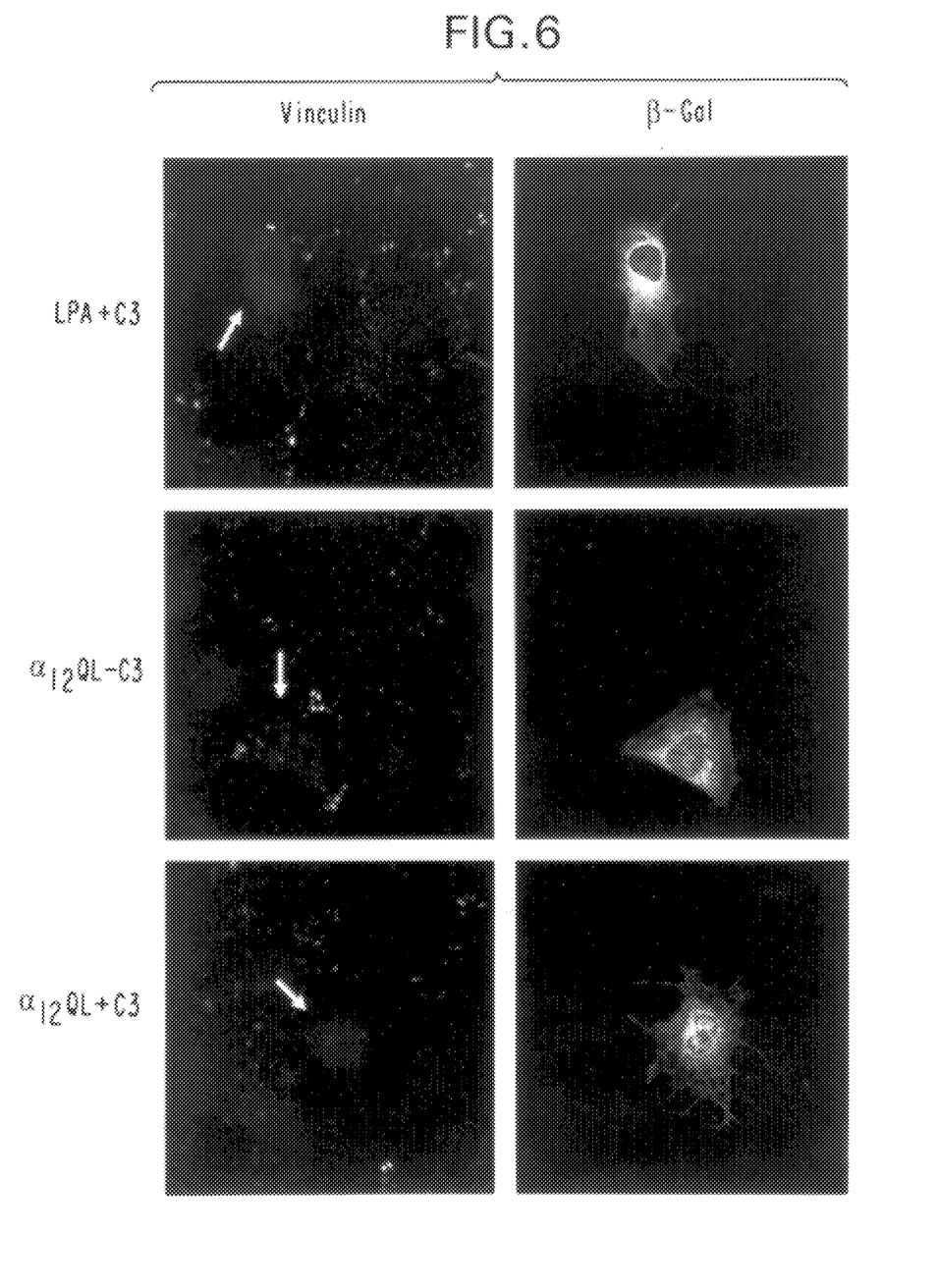
FIG. 6 illustrates focal adhesion assembly in Swiss 3T3 cells microinjected with an expression plasmid encoding constitutively activated $G_{\alpha 12}$ protein, in the presence or absence of botulinum C3 exoenzyme.

To determine the effect of botulinum C3 exoenzyme on focal adhesion assembly, samples of cells microinjected with botulinum C3 exoenzyme and α$_{12}$QL were treated with LPA (200 ng/ml) using the method described in Section A of this Example, fixed, permeabilized and labeled with anti-vinculin antibody and anti-β-galactosidase antibody using the methods described in Example 1. The effects of botulinum C3 exoenzyme on LPA stimulated α$_{12}$QL-dependent focal adhesion assembly are shown in FIG. 6. The results indicate that botulinum C3 exoenzyme inhibited LPA and α$_{12}$QL stimulated focal adhesion formation (FIG. 6). Uninjected cells in the upper panel responded to LPA with the assembly of focal adhesions while focal adhesions are absent in the botulinum C3 exoenzyme injected cell. In other experiments the botulinum C3 exoenzyme also inhibited α$_{13}$QL stimulated focal adhesion assembly (not shown).

Taken together, the foregoing experiments demonstrate that Gα$_{12}$ and Gα$_{13}$ regulate Rho dependent actin polymerization resulting in stress fiber formation and the assembly of focal adhesions. Thus, the results clearly demonstrate that α$_{12}$ and α$_{13}$ integrate heterotrimeric G protein-coupled receptors with the regulation of Rho. The results further indicate that G$_{\alpha12}$ and G$_{\alpha13}$ have similar ability to stimulate Rho-dependent stress fiber formation and focal adhesion assembly. Thus, G$_{\alpha12}$ and G$_{\alpha13}$ can interact with a common regulator regulating Rho activation.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

What is claimed is:

1. A method to identify compounds capable of regulating actin polymerization, stress fiber formation or focal adhesion assembly in a cell, comprising:

(a) contacting a cell with a putative regulatory compound, wherein said cell includes a Rho protein and a G protein that can regulate the activity of said Rho protein, said G protein selected from the group consisting of G$_{12}$ and G$_{13}$; and    (b) assessing the ability of said putative regulatory compound to regulate a biological function selected from the group consisting of actin polymerization, stress fiber formation or focal adhesion assembly.

2. The method of claim 1, wherein said assessment step comprises determining the ability of said G protein to regulate Rho protein activity in said cell.

3. The method of claim 1, wherein said assessment step comprises determining the ability of said G protein to regulate the activity of a Rho regulator molecule.

4. The method of claim 3, wherein said Rho regulator molecule is selected from the group consisting of a protein comprising a Dbl-homologous domain, a protein comprising a lbc-homologous domain, a Rho guanine nucleotide dissociation inhibitor and a Rho GTPase-activating protein.

5. The method of claim 3, wherein said Rho regulator molecule is selected from the group consisting of Dbl, Bcr, Vav, Ect2, Sos, RasGRF, RhoGDI, LyGDI, D4, RhoGAP, p190, 3BP1, n-chimaerin, β-chimaerin and p85.

6. The method of claim 1, wherein said assessment step comprises determining the GTP binding activity of said Rho protein.

7. The method of claim 1, wherein said assessment step comprises determining the GTP exchange activity of said Rho protein.

8. The method of claim 1, wherein said assessment step comprises the step of determining that said cell has been altered in a manner selected from the group consisting of alterations in adhesion, growth, shape and motility characteristics.

9. The method of claim 1, wherein said assessment step comprises the step of determining the extent of actin polymerization in said cell.

10. The method of claim 1, wherein said assessment step comprises determining focal adhesion kinase phosphorylation, paxillin phosphorylation and vinculin phosphorylation.

11. The method of claim 1, wherein said method further comprises stimulating said cell, prior to said assessing step, with a stimulatory compound capable of inducing a biological function selected from the group consisting of actin polymerization, stress fiber formation and focal adhesion assembly in said cell.

12. The method of claim 1, wherein said method further comprises stimulating said cell, prior to said assessment step, with a stimulatory compound selected from the group consisting of thrombin, gastrin-releasing protein, lysophosphatidate, C5a, IL-8, MIP1α, MIP1β, MCP-1, MCP-3, PAF, FMLP, LTB$_4$, RANTES, vasopressin, bradykinin and Substance P.

13. The method of claim 1, wherein said Rho protein is selected from the group consisting of Rho A, Rho B and Rho C.

14. The method of claim 1, wherein said cell is selected from the group consisting of a mammalian, an invertebrate, a plant, an insect, a fungal, a yeast and a bacterial cell.

15. The method of claim 1, wherein said cell is selected from the group consisting of a mammalian, an amphibian and a yeast cell.

16. The method of claim 1, wherein said cell is selected from the group consisting of a primate, a mouse and a rat cell.

17. The method of claim 1, wherein said cell is selected from the group consisting of a HELA, a fibroblast, a rat basophilic, a human eosinophil, a human endothelial, a human T cell, a human B cell, a human neutrophil, a human epithelial, a human macrophage, a Swiss 3T3, a melanocyte, a leukemia, a MonoMac6, a Rat 1a, an HEK 293, a KU812 and a BJAB cell.

18. The method of claim 1, wherein said cell comprises at least one class of cell surface receptor that initiates a biological function selected from the group consisting of actin polymerization, stress fiber formation or focal adhesion assembly upon binding of a stimulatory molecule to said receptor.

19. The method of claim 1, wherein said cell comprises a cell surface receptor selected from the group consisting of G protein-linked receptors, tyrosine kinase-linked receptors and receptors having ligand-gated ion channels.

20. The method of claim 1, wherein said cell comprises a cell surface receptor selected from the group consisting of a gastrin-releasing protein receptor, a thrombin receptor, a lysophosphatidate receptor, a C5aR, an IL-8R, a MIP1αR, a MIP1βR, a MCP-1R, a MCP-3R, a PAFR, a FMLPR, a LTB$_4$R, a RANTES receptor, a vasopressin receptor, a bradykinin receptor and a Substance P receptor.

21. The method of claim 1, wherein said cell comprises a cell surface receptor derived from a human cell.

22. The method of claim 1, wherein said putative regulatory compound is selected from the group consisting of a protein-based compound, a carbohydrate-based compound, a lipid-based compound, a nucleic acid-based compound, a natural organic compound, a synthetically derived organic compound, an anti-idiotypic antibody and/or catalytic antibody, or fragments thereof.

23. A regulatory compound identified by said compound's ability to regulate a biological function selected from the group consisting of actin polymerization, stress fiber formation or focal adhesion assembly in a cell, said compound being capable of penetrating the plasma membrane of a cell and of inhibiting the ability of a G protein to regulate Rho protein activity in said cell, wherein said compound is capable of regulating the activity of a G protein selected from the group consisting of $G_{\alpha 12}$ or $G_{\alpha 13}$.

24. The compound of claim 23, wherein said regulation involves a step selected from the group consisting of sequestering a $G_{\alpha 12}$ or a $G_{\alpha 13}$ protein in an inactive complex, regulating the nucleotide exchange region of a $G_{\alpha 12}$ or a $G_{\alpha 13}$ protein, regulating GTP hydrolysis by a $G_{\alpha 12}$ or a $G_{\alpha 13}$ protein, regulating a cell surface receptor interaction with a $G_{\alpha 12}$ or a $G_{\alpha 13}$ protein, regulating the interaction between a $G_{\alpha 12}$ or a $G_{\alpha 13}$ protein with a Rho regulator molecule, regulating the expression of endogenous or heterologous nucleic acid molecules encoding a $G_{\alpha 12}$ or a $G_{\alpha 13}$ protein, and combinations thereof.

25. A method to identify compounds capable of regulating actin polymerization, stress fiber formation or focal adhesion assembly in a cell, comprising:

(a) contacting a putative regulatory compound with a formulation comprising a Rho regulator molecule and a G protein capable of regulating the activity of said Rho regulator molecule, wherein said G protein is selected from the group consisting of $G_{\alpha 12}$ or a $G_{\alpha 13}$; and (b) assessing the ability of said putative regulatory compound to regulate the activity of said Rho regulator molecule.

26. The method of claim 25, wherein said step of assessing comprises determining the binding of said G protein to said Rho regulator molecule.

27. The method of claim 25, further comprising contacting a cell with said putative regulatory compound and assessing the ability of said compound to regulate a biological function selected from the group consisting of actin polymerization, stress fiber formation and focal adhesion assembly.

28. The method of claim 25, wherein said Rho regulator molecule is selected from the group consisting of Dbl, Bcr, Vav, Ect2, Sos, RasGRF, RhoGDI, LyGDI, D4, RhoGAP, p190, 3BP1, n-chimaerin, β-chimaerin and p85.

29. A method to inhibit a biological function selected from the group consisting of actin polymerization, stress fiber formation and focal adhesion assembly, comprising inhibiting the activity of a protein selected from the group consisting of $G_{\alpha 12}$ and $G_{\alpha 13}$.

30. The method of claim 29, wherein said activity being inhibited is selected from the group consisting of sequestering a $G_{\alpha 12}$ or a $G_{\alpha 13}$ protein in an active complex, regulating the nucleotide exchange region of a $G_{\alpha 12}$ or a $G_{\alpha 13}$ protein, regulating GTP hydrolysis by a $G_{\alpha 12}$ or a $G_{\alpha 13}$ protein, regulating a cell surface receptor interaction with a $G_{\alpha 12}$ or a $G_{\alpha 13}$ protein, regulating the interaction between a $G_{\alpha 12}$ or a $G_{\alpha 13}$ protein with a Rho regulator molecule, regulating the expression of endogenous or heterologous nucleic acid molecules encoding a $G_{\alpha 12}$ or a $G_{\alpha 13}$ protein, and combinations thereof.

31. The method of claim 29, wherein said activity is inhibited using a compound selected from the group consisting of a β subunit mimetope, a γ subunit mimetope, a Rho regulator mimetope, a G protein mimetope, a de-regulated protein kinase, a de-regulated G protein, a mutated G protein-coupled receptor, a G protein-coupled receptor agonist, a G protein-coupled receptor antagonist, G protein-coupled receptor reverse agonist, a nucleotide analog, an allosteric regulator of a G-coupled receptor, an antisense oligonucleotide, a ribozyme and an expression plasmid encoding $G_{\alpha 12}$ or $G_{\alpha 13}$.

32. A method to inhibit cell metastases, comprising inhibiting the activity of a protein selected from the group consisting of $G_{\alpha 12}$ or $G_{\alpha 13}$.

33. The method of claim 32, wherein said activity being inhibited is selected from the group consisting of actin polymerization, stress fiber formation and focal adhesion assembly.

34. The method of claim 32, wherein said activity being inhibited is selected from the group consisting of sequestering a $G_{\alpha 12}$ or a $G_{\alpha 13}$ protein in an active complex, regulating the nucleotide exchange region of a $G_{\alpha 12}$ or a $G_{\alpha 13}$ protein, regulating GTP hydrolysis by a $G_{\alpha 12}$ or a $G_{\alpha 13}$ protein, regulating a cell surface receptor interaction with a $G_{\alpha 12}$ or a $G_{\alpha 13}$ protein, regulating the interaction between a $G_{\alpha 12}$ or a $G_{\alpha 13}$ protein with a Rho regulator molecule, regulating the expression of endogenous or heterologous nucleic acid molecules encoding a $G_{\alpha 12}$ or a $G_{\alpha 13}$ protein, and combinations thereof.

35. The method of claim 32, wherein said activity is inhibited using a compound selected from the group consisting of a β subunit mimetope, a γ subunit mimetope, a Rho regulator mimetope, a G protein mimetope, a de-regulated protein kinase, a de-regulated G protein, a mutated G protein-coupled receptor, a G protein-coupled receptor agonist, a G protein-coupled receptor antagonist, G protein-coupled receptor reverse agonist, a nucleotide analog, an allosteric regulator of a G-coupled receptor, an antisense oligonucleotide, a ribozyme and an expression plasmid encoding $G_{\alpha 12}$ or $G_{\alpha 13}$.

36. A method to inhibit cell chemotaxis, comprising inhibiting the activity of a protein selected from the group consisting of $G_{\alpha 12}$ or $G_{\alpha 13}$.

37. The method of claim 36, wherein said activity being inhibited is selected from the group consisting of actin polymerization, stress fiber formation and focal adhesion assembly.

38. The method of claim 36, wherein said activity being inhibited is selected from the group consisting of sequestering a $G_{\alpha 12}$ or a $G_{\alpha 13}$ protein in an active complex, regulating the nucleotide exchange region of a $G_{\alpha 12}$ or a $G_{\alpha 13}$ protein, regulating GTP hydrolysis by a $G_{\alpha 12}$ or a $G_{\alpha 13}$ protein, regulating a cell surface receptor interaction with a $G_{\alpha 12}$ or a $G_{\alpha 13}$ protein, regulating the interaction between a $G_{\alpha 12}$ or a $G_{\alpha 13}$ protein with a Rho regulator molecule, regulating the expression of endogenous or heterologous nucleic acid molecules encoding a $G_{\alpha 12}$ or a $G_{\alpha 13}$ protein, and combinations thereof.

39. The method of claim 36, wherein said activity is inhibited using a compound selected from the group consisting of a β subunit mimetope, a γ subunit mimetope, a Rho regulator mimetope, a G protein mimetope, a de-regulated protein kinase, a de-regulated G protein, a mutated G protein-coupled receptor, a G protein-coupled receptor agonist, a G protein-coupled receptor antagonist, G protein-coupled receptor reverse agonist, a nucleotide analog, an allosteric regulator of a G-coupled receptor, an antisense oligonucleotide, a ribozyme and an expression plasmid encoding $G_{\alpha 12}$ or $G_{\alpha 13}$.

40. A method to treat an animal with a disease selected from the group consisting of cancer, respiratory distress syndrome, inflammatory bowel disease, Parkinson's disease, Alzheimer's disease and restenosis, said method comprising administering to an animal an effective amount of a therapeutic composition comprising a compound that regulates a biological function selected from the group consisting of actin polymerization, stress fiber formation or focal adhesion assembly, said compound being capable of penetrating the plasma membrane of a cell in said animal and of inhibiting the ability of a G protein selected from the group consisting of $G_{12}$ and $G_{13}$ to regulate Rho protein activity in said cell.

41. A method to identify compounds capable of regulating actin polymerization, stress fiber formation or focal adhesion assembly in a cell, comprising:

(a) contacting a cell with a putative regulatory compound, wherein said cell includes a Rho protein and a G protein that can regulate the activity of said Rho protein, said G protein selected from the group consisting of $G_{\alpha 12}$ or $G_{\alpha 13}$; and (b) assessing the ability of said putative regulatory compound to regulate a biological function selected from the group consisting of actin polymerization, stress fiber formation or focal adhesion assembly.

42. A kit to identify compounds capable of regulating actin polymerization, stress fiber formation or focal adhesion assembly, said kit comprising:

(a) a cell comprising a Rho protein and a G protein that can regulate the activity of said Rho protein, said G protein selected from the group consisting of $G_{12}$ and $G_{13}$; and (b) a means for detecting regulation of said Rho protein.

43. The kit of claim 42, wherein said cell is selected from the group consisting of a mammalian cell, an amphibian cell and a yeast cell.

* * * * *